United States Patent
Refai et al.

(10) Patent No.: US 11,419,491 B2
(45) Date of Patent: Aug. 23, 2022

(54) COLONOSCOPY SYSTEM AND METHOD

(71) Applicant: Optecks, LLC, Tulsa, OK (US)

(72) Inventors: Hakki Refai, Bixby, OK (US); Omar Yusef Kudsi, Chestnut Hill, MA (US); Badia Koudsi, Bixby, OK (US)

(73) Assignee: Optecks, LLC, Tulsa, OK (US)

( * ) Notice: Subject to any disclaimer, the term of this patent is extended or adjusted under 35 U.S.C. 154(b) by 39 days.

(21) Appl. No.: 16/801,992

(22) Filed: Feb. 26, 2020

(65) Prior Publication Data
US 2020/0281454 A1    Sep. 10, 2020

Related U.S. Application Data

(60) Provisional application No. 62/951,094, filed on Dec. 20, 2019, provisional application No. 62/852,149, (Continued)

(51) Int. Cl.
*A61B 1/00* (2006.01)
*A61B 1/31* (2006.01)
(Continued)

(52) U.S. Cl.
CPC ............ *A61B 1/31* (2013.01); *A61B 1/00006* (2013.01); *A61B 1/00009* (2013.01); (Continued)

(58) Field of Classification Search
CPC ... A61B 1/31; A61B 1/00006; A61B 1/00009; A61B 1/00016; A61B 1/00163; A61B 2562/0257; A61B 2034/2055; A61B 2034/2065; A61B 1/00172; A61B 1/00174; A61B 1/00183; A61B 1/0019; (Continued)

(56) References Cited

U.S. PATENT DOCUMENTS

2011/0301447 A1* 12/2011 Park ................. G06T 7/0016
                                                     600/407
2013/0342756 A1   12/2013 Xu et al.
(Continued)

FOREIGN PATENT DOCUMENTS

WO    WO 2019/104329 A1    5/2019

OTHER PUBLICATIONS

Schmalz et al., "An endoscopic 3D scanner based on structured light." Medical Image Analysis, 2012, pp. 1063-1071 [online] <https://www.researchgate.net/publication/224866113_An_endoscopic_3D_scanner_based_on_structured_light>.
(Continued)

*Primary Examiner* — Timothy J Neal
(74) *Attorney, Agent, or Firm* — Dunlap Codding, P.C.

(57) ABSTRACT

Described are colonoscopy systems and methods of using such systems. The colonoscopy systems may include an optical scanning system having at least one illuminator configured to produce spatially patterned light and solid light in at least one frame to illuminate tissue within the colon, and at least one camera configured to capture the at least one image of the illuminated tissue within the colon. Additionally, the optical scanning system may include at least one control system configured to construct at least one three dimensional point cloud representations of the tissue within the colon.

22 Claims, 21 Drawing Sheets

Related U.S. Application Data filed on May 23, 2019, provisional application No. 62/810,784, filed on Feb. 26, 2019.

(51) Int. Cl.
  *A61B 1/06* (2006.01)
  *A61B 90/00* (2016.01)

(52) U.S. Cl.
  CPC ...... *A61B 1/00016* (2013.01); *A61B 1/00163* (2013.01); *A61B 1/0638* (2013.01); *A61B 90/39* (2016.02); *A61B 2562/0257* (2013.01)

(58) Field of Classification Search
  CPC ... A61B 1/0638; A61B 1/0646; A61B 1/0661; A61B 5/0086; A61B 2034/2046; A61B 5/0073; A61B 2576/02; A61B 2562/0238; A61B 1/00055; A61B 2562/0242; G01N 21/00; G06T 2207/10068; G06T 2207/10076
  See application file for complete search history.

(56) References Cited

U.S. PATENT DOCUMENTS

| | | | |
|---|---|---|---|
| 2014/0323878 A1 | 10/2014 | Toriumi et al. | |
| 2016/0073928 A1 | 3/2016 | Soper et al. | |
| 2016/0360954 A1* | 12/2016 | Rohling | A61B 34/20 |
| 2017/0100024 A1* | 4/2017 | Shah | G02B 23/26 |
| 2017/0280970 A1 | 10/2017 | Sartor et al. | |
| 2018/0253839 A1 | 9/2018 | Zur | |
| 2018/0292200 A1* | 10/2018 | Mor | G06F 3/042 |
| 2018/0296281 A1* | 10/2018 | Yeung | A61B 34/32 |

OTHER PUBLICATIONS

International Search Report and Written Opinion (PCT/US20/19908); dated Jun. 11, 2020; 9 pgs.

\* cited by examiner

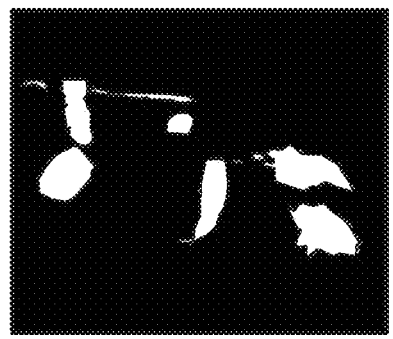 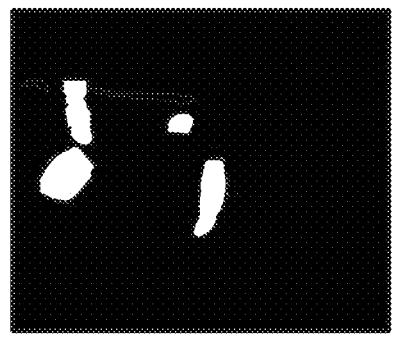
FIG. 22A  FIG. 22B
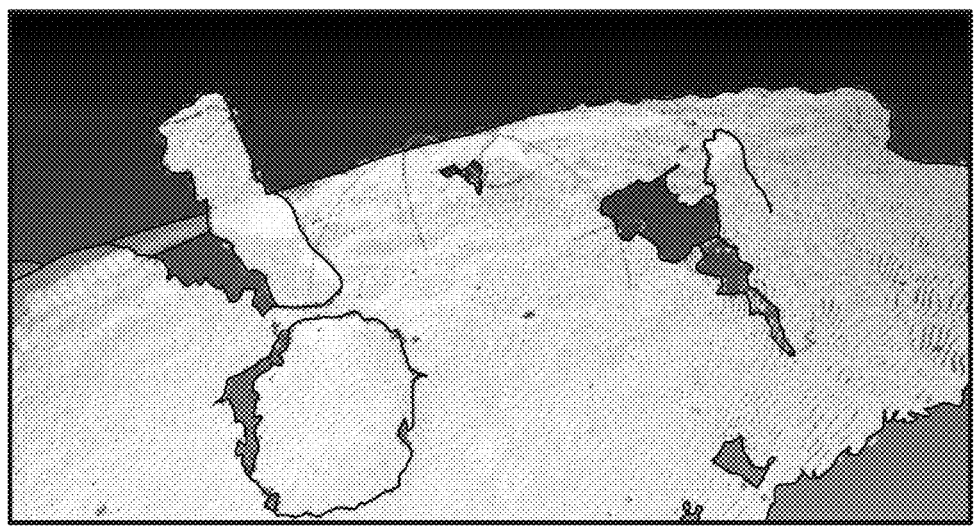
FIG. 23
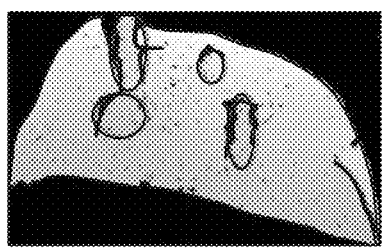 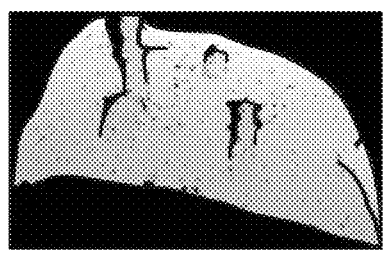 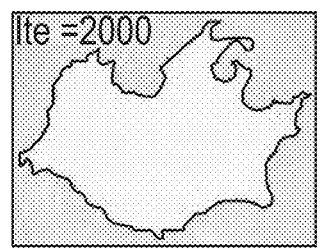
FIG. 24A  FIG. 24B  FIG. 24C

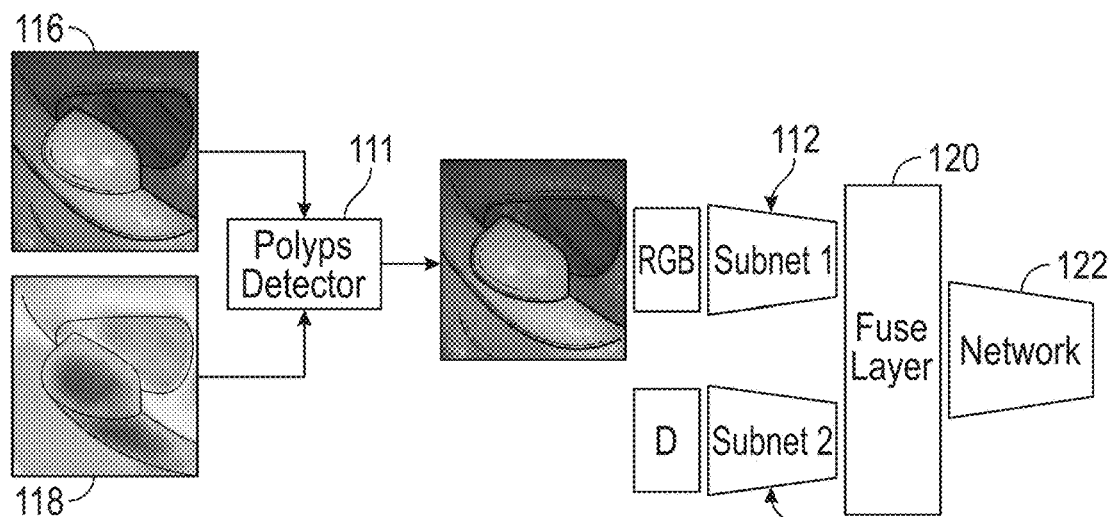
FIG. 25
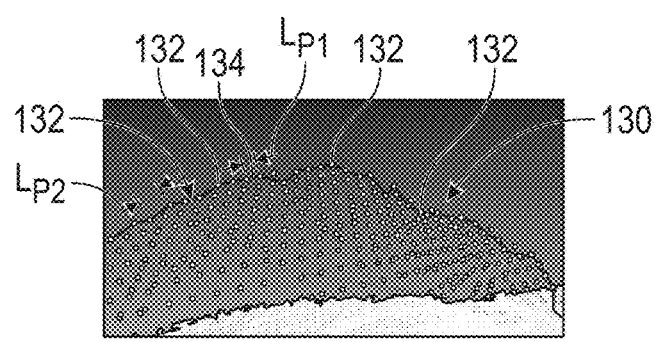
FIG. 26
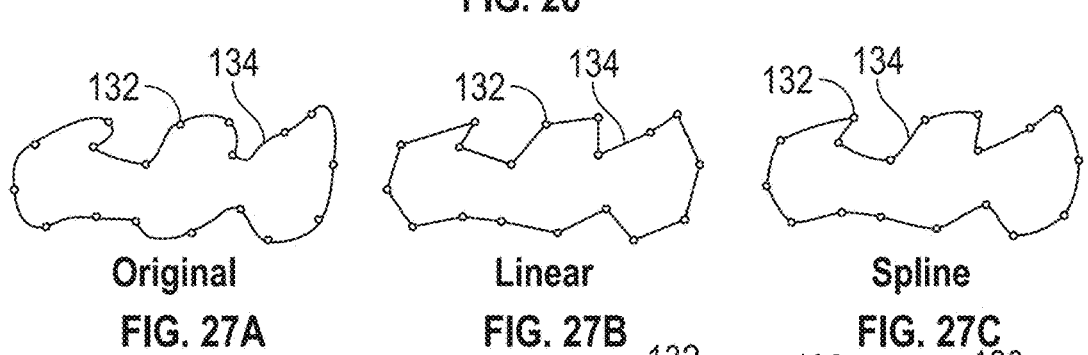
Original
FIG. 27A
Linear
FIG. 27B
Spline
FIG. 27C
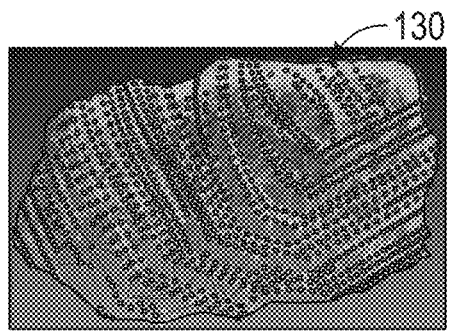
FIG. 28A
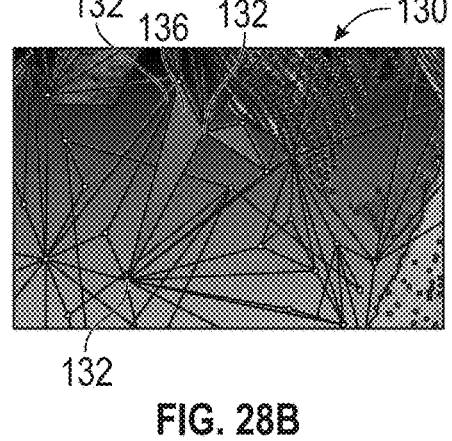
FIG. 28B Frame i Frame i+1

COLONOSCOPY SYSTEM AND METHOD

INCORPORATION BY REFERENCE

The present patent application claims priority and benefit of Provisional U.S. Ser. No. 62/951,094, filed Dec. 20, 2019; which claims priority and benefit of Provisional U.S. Ser. No. 62/852,149, filed May 23, 2019, which claims priority and benefit of Provisional U.S. Ser. No. 62/810,784, filed Feb. 26, 2019; the entire contents of all of which are hereby incorporated herein by reference.

BACKGROUND

Colonoscopy provides a gold standard screening tool in the battle to detect and prevent colorectal cancer (CRC), the second leading cancer-related killer in the U.S.; yet, even trained gastroenterologists regularly miss polyps and adenomas that may lead to colorectal cancer. A study of back-to-back colonoscopy procedures found miss rates of 16.8% for polyps and 17.0% for adenomas, increasing to 20.7% and 22.9% for small (<6 mm) polyps and adenomas respectively, even when performed by experienced personnel [1,2]. Including all procedures, anywhere from 3% to 5.5% of missed polyps become cancerous growths [1,3], and 6% of patients develop CRC within three years of a clear colonoscopy. A shortage of endoscopy specialists and an ever-increasing over-50 population compound the problem. In 2010, gastroenterologists performed just about 50% of colonoscopies [4], and studies clearly show that inexperienced practitioners are five times more likely to miss polyps and adenomas than experienced practitioners [3, 5]. In 2013, only 58% of adults 50-75 remained up to date on screenings for CRC [6], driven in part by lack of access to experienced endoscopic practitioners. Missed polyps, adenomas, and cancers have direct consequences in both lives and medical costs. Nearly 150,000 people are diagnosed with colorectal cancer every year, and 35% of CRC patients die from the condition [7]. In 2010, direct medical costs for CRC care exceeded $14 billion [8], and projected costs for 2020 may exceed $17 billion [9]. Detecting CRC at stage I instead of stage IV saves lives and reduces treatment costs by 27% [9,10]. Reducing the gap between needed screenings and available professionals would require over 7300 additional trained specialists [4], a professional population which current and projected medical school graduation rates cannot possibly meet. A safe, accurate, efficient, and augmented tool readily installed on the endoscopic instrument and easily employed by both specialists and non-specialists may significantly improve accuracy and success rates of colonoscopy, increase efficiency to reduce procedure times, and improve patient access to screenings, leading to earlier detection and more effective treatment of CRC.

Existing colonoscopy systems utilize technology developed over ten years ago that limits operator effectiveness in detecting abnormal tissue. Standard endoscopes utilize a visible light source and camera to view the colon. The operator can insert additional instruments through the endoscope tip to perform a polypectomy or collect samples from potentially cancerous tissues. Ideally, current colonoscopy techniques can find precancerous polyps and adenomas, facilitate removal or treatment, and provide early detection of CRC. The CDC estimates that colonoscopies prevented 66,000 colorectal cancers between 2003 and 2007 alone [8,10]. Despite the endoscope's capabilities and operator training, operators still miss polyps and adenomas that can lead to interval cancers. Missed polyps and adenomas occur for several reasons. Polyps and adenomas, particularly ones under 6 mm in size, can grow in folds in the colon wall that block the operator's view. Abnormal tissue can have similar coloring to that of surrounding tissue, reducing visual contrast, causing abnormal tissue to blend into the background. The miss rate increases as the number and density of polyps increases. Other causes include poor bowel preparation, failure to examine the colon through to the cecum, and executing the procedure too quickly, which can result in poor positioning of the camera, resulting in sections of the colon going unscreened. Improving the efficacy of colonoscopy procedures therefore requires development of new technologies and non-traditional systems that provide better tissue scanning and physician guidance.

Several proposed solutions within the prior art, such as narrowband imaging, autofluorescence, virtual colonoscopy, and Third-Eye® retroscope [11-14] have proceeded as far as clinical trials. In all of these methods, clinical trials found the increase in adenoma detection was statistically insignificant and in some cases nonexistent, and what significant difference did exist in one trial or set of patients could not be consistently maintained over successive trials. Several companies developed, tested, and commercialized systems that attempted to improve the efficacy of colonoscopy procedures. The Endocuff, G-EYE, and EndoRings solutions employ mechanical systems that protrude from the endoscope's tip to flatten colon folds that may hide polyps and adenomas [15-17]. In interviews, physicians reported that the protrusions made inserting the endoscope into the patient difficult, complicated endoscope movement, increased procedure length, and increased potential to injure or perforate the colon [14]. The Third Eye Panoramic System employs a module containing two side facing, wide angle source-camera pairs mounted on the endoscope's side [18]. The system displays three separate images on the screen, one per camera, requiring the operator to simultaneously monitor and process three images to detect polyps instead of a single, integrated view. The viewing difficulty, and lack of detection, location, and treatment assistance, does not significantly increase polyp detection rate. Magnetiq Eye employs deep-learning artificial intelligence (AI) techniques to examine 2D video endoscope images and identify suspicious tissue based on extensive training. The effectiveness of detecting missed adenomas depends strongly on the quality and extent of AI training data. Such methods have been demonstrated to perform poorly, even when well trained, when working in an environment such as the colon that produces featureless two dimensional images, limiting effective reduction in miss rates. The artificial intelligence also produced a very high rate of false positives for detected polyps using only two dimensional images for input.

A commercial system exists that employs three dimensional magnetic endoscopic imaging, using external sensors to track a magnetic marker on the endoscope, to help the operator locate the endoscope within the patient's colon with millimeter accuracy. Tracking endoscope position allows identification and real-time treatment of colon loops [19,20]. However the system cannot detect polyps and adenomas, cannot provide navigation guidance or other operator assistance, and does not miniaturize well. The limitations of proposed and commercially available technologies highlight the need for an approach that integrates seamlessly with the endoscope to minimize hindrance to the surgical procedure, provides accurate and easy-to-use information to the performing physician, and demonstrates improved detection and treatment of polyps, adenomas, and cancerous tissue.

Optical scanning systems offer a candidate technology for producing high-accuracy three dimensional imagery and modeling of the colon. Current commercially available three dimensional optical scanners utilize a combination of technologies, including near-infrared (NIR) and visible light, digital light projection (DLP) sources and vertical cavity surface emitting laser (VCSEL) projectors, and high-resolution cameras, to produce three dimensional scans of an object. However, all currently available scanners are designed to operate in an environment that does not restrict the distance between scanner and object. In such an environment, the scanner typically uses a large (≥8 cm) baseline—the distance between centers of the optical source and/or recording cameras—to achieve high resolution depth measurements [26-33]. The environment does not restrict source and/or camera size, and thus the systems use larger (dimensions up to 1 cm) components, particularly for the cameras, to increase field of view and depth accuracy. However, scanning and measurement operations in the human body severely limit distance between scanner and object and severely restrict scanning system size. In the colon, 5 cm at most separates a wall from center, which precludes the use of long baselines and large components. Systems with larger dimensions and components would not integrate well with the endoscope, most likely resulting in protrusions or separate systems that would hinder the procedure in much the same manner as mechanical solutions.

BRIEF DESCRIPTION OF THE SEVERAL VIEWS OF THE DRAWINGS

To assist those of ordinary skill in the relevant art in making and using the subject matter hereof, reference is made to the appended drawings, which are not intended to be drawn to scale, and in which like reference numerals are intended to refer to similar elements for consistency. For purposes of clarity, not every component may be labeled in every drawing.

FIGS. 22A and 22B are binary maps obtained via binary processing and an associated filtered binary map indicating one or more possible polyp sites areas and one or more non-possible polyp site areas.

FIG. 23 is a projection of a filtered distance map onto a three dimensional point cloud.

FIGS. 24A-24C illustrate an exemplary keypoint detection process in accordance with the present disclosure.

FIG. 25 is a block diagram of an exemplary method of polyp detection and/or measurement for a colonoscopy system having the optical scanning systems of FIG. 18 or 19.

FIG. 26 is a three dimensional point cloud with data points located on a polyp border and lines connecting border data points to determine perimeter of a polyp.

FIGS. 27A-27C are data points describing exemplary methods for determining perimeter of a polyp in accordance with the present disclosure.

FIGS. 28A and 28B is an image of a mesh constructed from a three dimensional point cloud along a surface of a polyp and triangulation to aid in measuring surface area of the polyp, respectively.

DETAILED DESCRIPTION

Figure 1:
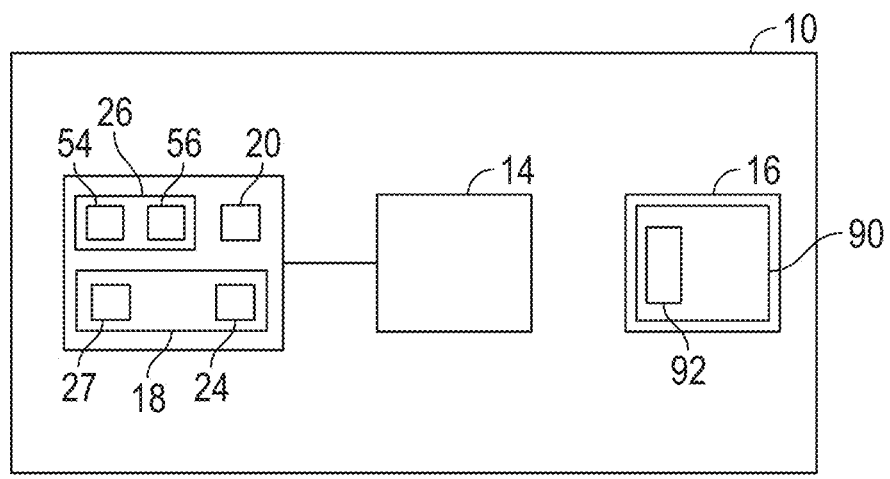
FIG. 1 is a block diagram of an exemplary colonoscopy system having an optical scanning system, an AHRS unit, and a control system in accordance with the present disclosure.

As described in further detail herein, in some embodiments, model-building capabilities of three-dimensional optical scanners and two-dimensional imaging methods are used, in addition to, novel polyp detection software, with all hardware miniaturized to fit within a standard endoscope's dimensions. In some embodiments, miniature laser arrays, pattern and solid illumination generation, NIR cameras, and advanced processing algorithms are configured to meet size, mapping speed, and accuracy needs of colonoscopy procedures.

In some embodiments, optical scanning systems may include one or more near infrared (NIR) cameras and one or more NIR VCSEL sources integrated within an end of an endoscope (i.e., endoscopic hardware). Employing NIR sources and cameras takes advantage of the high NIR reflectivity of tissue to produce high resolution recordings without interfering with the endoscope's existing visual systems. Each VCSEL source may occupy an area less than 5 $mm^2$, for example. Each camera may occupy an area less than 12 $mm^2$, for example, such that components are configured to fit within the exemplary endoscope's 12.8 mm diameter. The 1- to 5-cm working distance within the colon, combined with small component size and the capabilities of software, allow the system to operate on a 5.5 mm baseline and still achieve sub-millimeter or millimeter measurement accuracy in depth.

The optical sources may be configured to produce both patterned light (intensity variations over space) and solid illumination (no intensity variation over space). Patterned light illumination of the colon wall, combined with stereoscopic vision provided by using one or more cameras, may produce data that allows the software to accurately locate each part of the colon in three-dimensional space, producing a three-dimensional point cloud consisting of the collection of three-dimensional points identified from the imaging data provided by the cameras.

The imaging and processing software may be configured to construct the three-dimensional point clouds and three-dimensional models of colon sections with sub-millimeter or millimeter accuracy. Software algorithms implement polyp/adenoma detection functions that allow detection of polyps of any sizes including those equal to or below 6 mm, even when polyp/adenoma coloring closely matches the coloring of the colon wall. The solid illumination NIR source accentuates the contrast between blood vessels and surrounding tissue in the colon wall providing a unique 2D topography, for example. As such, the software may be configured to perform pattern matching between images to extract registration information (tilt and shift between successive images) to extract features from the otherwise featureless colon wall and combining three-dimensional point clouds into a single, integrated three dimensional model of the entire colon, for example.

Combining three-dimensional and two-dimensional imaging capabilities may allow the software to accurately locate polyps within the colon, detect colon loops, detect when the operator does not fully scan a colon section, precisely and/or accurately localize one or more tumors (e.g., for follow-up surgical treatment), detect areas within the colon where operator missed areas of interest, and/or create a record for tracking a patient's colon health.

Before explaining at least one embodiment of the disclosure in detail, it is to be understood that the disclosure is not limited in its application to the details of construction, experiments, exemplary data, and/or the arrangement of the components set forth in the following description or illustrated in the drawings unless otherwise noted.

The disclosure is capable of other embodiments or of being practiced or carried out in various ways. Also, it is to be understood that the phraseology and terminology employed herein is for purposes of description, and should not be regarded as limiting.

The following detailed description refers to the accompanying drawings. The same reference numbers in different drawings may identify the same or similar elements.

As used in the description herein, the terms "comprises," "comprising," "includes," "including," "has," "having," or any other variations thereof, are intended to cover a non-exclusive inclusion. For example, unless otherwise noted, a process, method, article, or apparatus that comprises a list of elements is not necessarily limited to only those elements, but may also include other elements not expressly listed or inherent to such process, method, article, or apparatus.

Further, unless expressly stated to the contrary, "or" refers to an inclusive and not to an exclusive "or". For example, a condition A or B is satisfied by one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or more, and the singular also includes the plural unless it is obvious that it is meant otherwise. Further, use of the term "plurality" is meant to convey "more than one" unless expressly stated to the contrary.

As used herein, any reference to "one embodiment," "an embodiment," "some embodiments," "one example," "for example," or "an example" means that a particular element, feature, structure or characteristic described in connection with the embodiment is included in at least one embodiment. The appearance of the phrase "in some embodiments" or "one example" in various places in the specification is not necessarily all referring to the same embodiment, for example.

Referring to the Figures, and in particular FIG. 1, shown therein and designated by reference numeral 10 is an exemplary colonoscopy system in accordance with the present disclosure. Generally, the colonoscopy system 10 is an intra-operative, dynamic three-dimensional scanning system configured to detect, measure and/or locate polyps and/or adenomas within a colon. In some embodiments, the colonoscopy system 10 may include real time measurement data capable of providing guidance and/or positioning of one or more tools for treatment and/or removal of polyps and/or adenomas of the colon. In some embodiments, the colonoscopy system 10 may provide real-time scanning and processing supports for augmented navigation guidance for optimal driving and positioning of an endoscope. In some embodiments, the colonoscopy system 10 may include real-time mapping and registration configured to provide three-dimensional model(s) supporting loop detection and/or monitoring of health of a patient. It should be noted that the colonoscopy system 10 as described in detail herein may be a stand-alone system or integrated with current standard colonoscopy systems known within the art.

The colonoscopy system 10 is configured to provide three-dimensional point clouds with sub-millimeter or more (e.g., millimeter) accuracy during a colonoscopy procedure and/or subsequent to the colonoscopy procedure. The colonoscopy system 10 is configured to use unique patterns of blood vessels within the colon to extract information and position from frame to frame and accurately stitch the three-dimensional point clouds into a three-dimensional model of the colon. Additionally, by processing data within the three-dimensional point cloud and the three-dimensional model, augmented navigation guidance may be provided allowing a user to position and/or direct the colonoscopy system 10 within the colon. Such guidance may improve likelihood of full cecal intubation ensuring scanning of the entire colon and increase success rate of the colonoscopy procedure. Additionally such guidance may provide detection of colon loops, marking locations of cancerous tissue requiring surgical removal and/or treatment, provide input data to one or more control systems for semi-autonomous and autonomous colonoscopy procedure, and/or detailed documentation of one or more steps of the procedure providing information for continued prevention and/or treatment of colorectal cancer and/or issues of the colon.

The colonoscopy system 10 is configured to detect and/or measure polyps and/or adenomas. Additionally, in some embodiments, the colonoscopy system 10 is configured to alert an operator based on analysis of generated three-dimensional point clouds.

Generally, the colonoscopy system 10 may be used as a stand-alone system or a system integrated into currently used and future envisioned medical systems. In some embodiments, the colonoscopy system 10 may be integrated within systems including, but not limited to, Olympus, Boston Scientific, and Auris, for example. Additionally, the colonoscopy system 10 may be adapted for use in other procedures including, but not limited to, upper endoscopy, robotic or laparoscopic surgery autonomous and semi-autonomous surgical procedures, surgical safety systems, and the like.

Referring to FIG. 1, the colonoscopy system 10 includes an optical scanning system 12, an optional attitude and heading reference system (AHRS) unit 14, and a control system 16. Generally, the optical scanning system 12 illuminates tissue in walls of a colon and captures one or more images of the illuminated tissue. The AHRS unit 14 provides orientation and angular velocity (i.e., roll, pitch and yaw) data as a function of time to assist mapping and registration functions. The control system 16 processes the one or more images captured by the optical scanning system 12 and performs functions including, but not limited to, (1) detection and/or measurement of polyps and/or adenomas within the colon, (2) construction of one or more three-dimensional models and/or mappings of the colon for loop detection and other functions, (3) augment existing displays with data, symbols, icons, and/or other indicators to direct an operating physician in treating polyps and/or adenomas and/or in driving an endoscope through the colon; (4) providing data for semi-autonomous or autonomous control and/or operation of the endoscope during a colonoscopy procedure; (5) providing loop detection and/or treatment; and/or (6) providing detection of localized cancerous spots and/or unvisualized spots.

During a colonoscopy, generally an operating physician inserts a flexible endoscope (i.e., endoscopic hardware) into an anus and steers the flexible endoscope to observe state of health of a colon and possibly perform small surgical procedures to address problems such as the presence of polyps and adenomas observed during the procedure. 3. The AHRS unit 14 provides orientation and angular velocity (yaw, pitch, and roll) data regarding the movement of the optical scanning system 12. The AHRS unit 14 includes, but is not limited to, (a) an inertial measurement unit (IMU) and an ASIC; (b) an IMU connected to an external microprocessor by electronic cabling connecting the optical scanning system 12 to external power and processing systems, or the like.

Figure 2A:
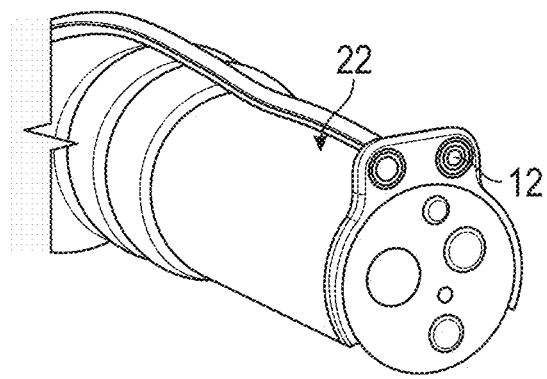
FIGS. 2A and 2B are perspective views exemplary endoscopic systems having exemplary optical scanning systems mounted on an outer wall.
Figure 2B:
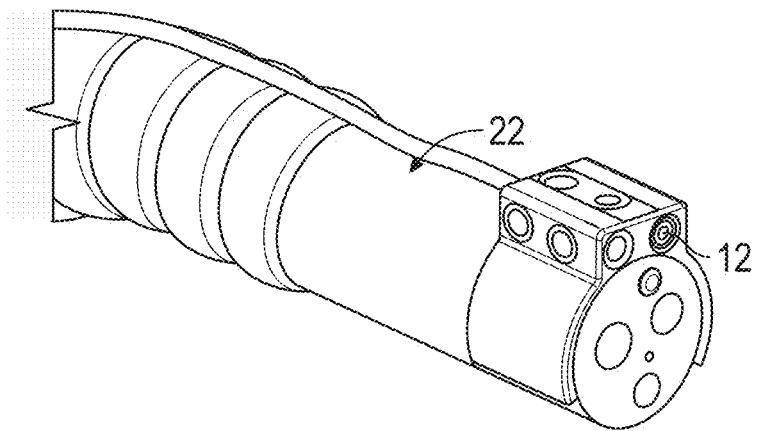
Figure 3:
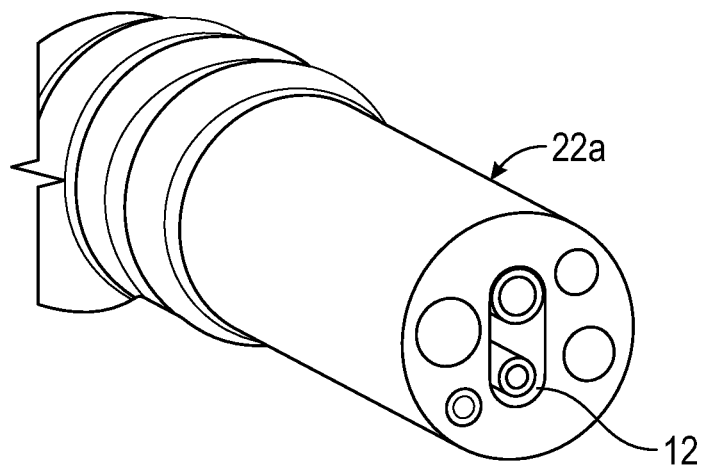
FIG. 3 is a perspective view of an exemplary endoscopic system having an exemplary optical scanning system integrated within hardware of the endoscopic system.

Referring to FIGS. 2A, 2B and 3, in some embodiments, one or more optical scanning systems 12 may mount on an outer wall an endoscopic instrument 22 (e.g., near the head of the endoscope), as illustrated in FIGS. 2A and 2B, and/or one or more optical scanning systems 12 may integrate directly into hardware of an endoscopic instrument 22a, as illustrated in FIG. 3. Endoscopic instrument 22a may herein be referred to as 'endoscopic hardware'. In some embodiments, the optical scanning system 12 may be mounted on a ring circumferentially fitted about an external circumference of a head of the endoscopic instrument. Further, cabling along the internal and/or external length of the endoscope instrument 22 may connect the optical scanning system 12 to one or more external physical and/or software components. It should be noted that the optical scanning system 12 may maintain a wired and/or wireless connection to one or more external physical and/or software components including, but not limited to, the AHRS unit 14, the control system 16, and/or any other system regardless of whether the system is positioned on the endoscopic instrument 22 or 22a, or positioned outside the body of a patient.

Each optical scanning system 12 may include one or more illuminator(s) 18, one or more camera(s) 20, and a control system 26. Generally, the one or more illuminator(s) 18 includes one or more optically-based pattern generator(s) 24 configured to impose spatial intensity and/or wavelength variation on light provided by one or more optical source(s) 27. The camera 20 records an image of light projected onto surface of tissue, and the control system 26 synchronizes the optical source(s) 27, camera(s) 20 and optically based pattern generator(s) 24. It should be noted that the control system 26 may be integrated into control system 16 based on design considerations.

The optical source(s) 27 may operate within infrared spectrum, UV spectrum and/or visible spectrum. For simplicity of description, the following embodiments describe use of infrared spectrum, however, it should be understood by one skilled in the art that an infrared, visible or both visible and infrared optical source(s) 27 may be used within the colonoscopy system 10. Further, the camera(s) 20 may be an infrared camera, visible and/or multispectral cameras.

Generally, the optical scanning system 12 is configured to illuminate one or more areas of interest within the colon with one or more optical light source(s) 27. Each optical source 27 may deliver significant optical power to the tissue under investigation without causing damage to the target tissue or the patient due to heating or interactions with high optical intensities. In some embodiments, the optical source 27 may include a laser diode, for example, operating in, but not limited to, the infrared region of the optical spectrum. Other diodes may be used operating in visible, or possibly both infrared and visible spectrums. For example, an operating region for the optical source 27 may be, but is not limited to, the near infrared (NIR) range between 700 nm and 1050 nm. In some embodiments, wavelengths may include 780 nm, 808 nm, 850 nm, or 940 nm as these wavelengths are available in commercial sources, provide maximum optical reflection from biological tissue, and are sufficiently far from the visible light region of the optical spectrum to avoid interfering with a visible light camera that may be used by endoscopic systems (e.g., endoscopic instrument 22 illustrated in FIGS. 2A and 2B) used in colonoscopy. The optical source 27 may provide sufficient power for the reflection from the tissue to be captured with sufficient contrast by the camera 20, but low enough power to avoid harm to the patient or to saturate the sensors used in the camera 20.

In some embodiments, the optical source 27 may deliver optical power to a target tissue via an optical fiber, liquid light guide or similar waveguide positioned about a side wall of an endoscopic instrument and terminating at the optical scanning system 12. In some embodiments, a large-core optical fiber may be used. Such large-core optical fiber may be configured to provide required power without damage to the optical fiber and use a minimum of cladding to limit physical dimensions so as to fit within an existing endoscopic instrument (e.g., endoscopic instrument 22 illustrated in FIG. 2). A large core optical fiber makes the optical fiber highly multimode, ensuring that the power distribution over the optical fiber may be nearly uniform. In some embodiments, a fused array of fibers or a shaped glass or plastic tube may be used.

In some embodiments, at least one end of the optical fiber may be formed as a flat surface or as a curved surface. A curved surface could include, but is not limited to, having a spherical or parabolic shape, for example. A curved surface shape may enhance a range of angles over which the optical fiber illuminates the target area, thereby increasing the size of the measurement area. A larger area may mean fewer images needed and/or more overlapping sections between successive images (e.g., improve stitching of images, improve accuracy/resolution).

In some embodiments, the optical source 27 may deliver optical power via a laser diode source positioned at the optical scanning system 12, powered through electrical cable strung from an external power supply through or along the side of the endoscopic instrument to the optical source 27. Possible sources include, but are not limited to, any infrared laser diode, including an edge-emitting laser (EEL) or a vertical cavity surface emitting laser (VCSEL). The VCSEL-based source may include, but is not limited to, a single VCSEL or a patterned array of VCSEL sources, the latter of which contributes directly to the generation of spatial intensity patterns on the tissue under investigation. In some embodiments, the optical source 27 and/or optical scanning system 12 may include mechanisms for mitigating heat.

Figure 4A:
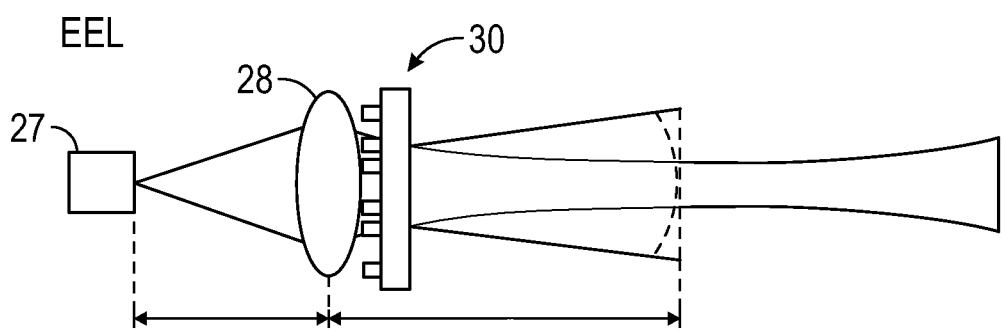
FIG. 4A is a block diagram of an exemplary optical imaging system collecting light from an edge-emitting laser (EEL), and an optically based pattern generator having a diffractive optical element positioned after the optical imaging system.
Figure 4B:
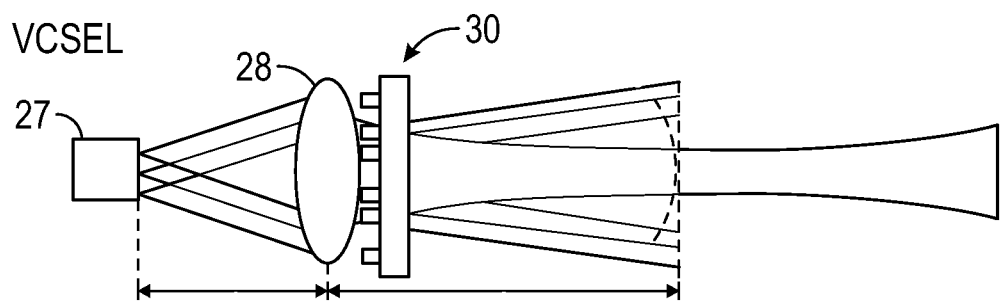
FIG. 4B is a block diagram of an exemplary optical imaging system collecting light a vertical cavity surface emitting laser (VCSEL), and an optically based pattern generator having a diffractive optical element positioned after the optical imaging system.

Referring to FIGS. 4A and 4B, in some embodiments, the illuminator 18 may include the optical source 27 and the optically-based pattern generator having an optical imaging system 28 and/or a diffractive optical element 30. It should be noted that in some embodiments, the illuminator 18 may solely include the optical source 27.

The optical imaging system 28 collects light from the optical source 27 and controls divergence and convergence of optical beams as each optical beam passes through the optically-based pattern generator 24. The optical imaging system 28 may include, but is not limited to, a single convex lens or a combination of two or more convex and/or concave lenses, projection optics, micro-optical elements, single optical element(s), meniscus lens, or combinations of two or more optical elements, convex lens, meniscus lens and/or concave lenses. In some embodiments, the focal length of the optical imaging system 28 may be selected to produce a primary imaging point at the average distance between the illuminator 18 and/or camera 20 and a wall of the colon, for example, typically around 3 cm, and to produce a long depth of focus, in some embodiments extending between 1 cm and 5 cm, to allow projection of sharp, high-contrast images for a range of distances between the optical scanning system 12 and/or camera 20 and the colon wall. In some embodiments, focal lengths minimize the distance between the optical source 27 and the optical imaging system 28 to minimize the size (in depth) of the illuminator 18 to facilitate integration with or mounting on the endoscope (e.g., endoscope instrument 22 illustrated in FIGS. 2A and 2B).

The optically-based pattern generator 24 may be configured to provide structured light and/or unstructured (i.e., unpatterned, flood, flat-top illumination or solid) illumination, and/or combinations thereof. For clarity in description, a structured light source is herein defined as a source configured to produce an optical light beam containing purposeful spatial variations in optical intensity. An unstructured light source, flood, flat-top illumination pattern or solid illumination light source is defined as a source configured to produce nearly constant illumination intensity over an area or range of angles. Generally, the optically-based pattern generator 24 may impose spatial intensity variation on the optical beam produced by the combination of the optical source 27 and the optical imaging system 28.

Referring to FIGS. 4A and 4B, in some embodiments, the optically-based pattern generator 24 may include the diffractive optical element (DOE) 30 positioned after the optical imaging system 28 at a distance selected to produce a specific pattern with specific spatial variation at the primary imaging point, including composite images consisting of both patterned and unpatterned sections, as shown in FIGS. 4A and 4B for both the edge-emitting laser (EEL) and vertical cavity surface emitting laser (VCSEL) optical sources 27. In some embodiments, the optically-based pattern generator 24 may include the diffractive optical element (DOE) positioned before the optical imaging system 28. The DOE 30 may include, but is not limited to, (a) surface height variations, such as etched gratings, and/or (b) variations in refractive index within the base material, such as holographic elements. For the VCSEL-based embodiment in FIG. 4B, the optical source 27 includes an array of VCSELs, with the arrangement of VCSELs chosen in combination with the DOE 30 to produce a pattern consisting of the convolution between the patterned-VCSEL array and the spatial variations in the DOE 30.

Figure 5A:
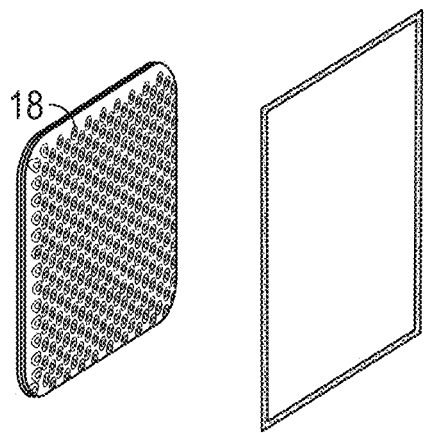
FIGS. 5A-5C are perspective views of exemplary projected patterns from optical sources without inclusion of diffractive optical elements.
Figure 5B:
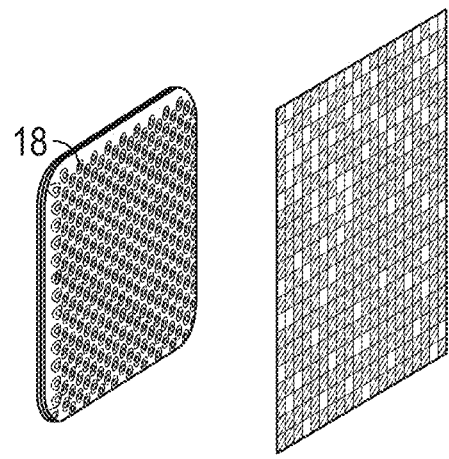
Figure 5C:
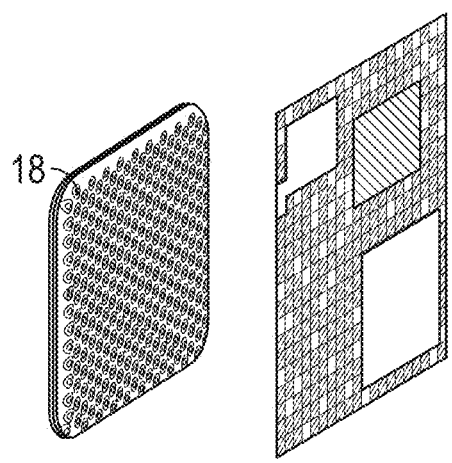

Referring to FIGS. 5A-5C, in some embodiments, the illuminator 18 includes optical source 27 that is an array of VCSELs, optical imaging system 28 and/or diffractive optical element 30 and illuminates the tissue. In some embodiments, the optical source 27 as an array of VCSELs is driven by a constant drive current, producing almost the same optical power over the full emitted optical beam, and the pattern of light illuminating the tissue is created by the special variations in the diffractive optical element 30. Solid (unpatterned) light results from a spatial variation in the diffractive optical element 30 that redistributes the optical power from the optical source 27 as the array of VCSELs such that the optical power remains constant or nearly constant over the illuminated area as shown in FIG. 5A. Composite images containing both patterned and unpatterned components result from a spatial variation in the diffractive optical element 30 which produces constant or nearly constant power (unpatterned) over some fraction of the illuminated area and produces specific variations (patterned) in optical power over remaining fraction of the illuminated area as shown in FIG. 5C. An alternative method of producing solid, patterned, or composite illumination include controlling the drive current to each VCSEL individually, thereby controlling the optical power output at each point in the VCSEL array. Solid (unpatterned) light results from operating all of the VCSELs at the same optical power as shown in FIG. 5A. Composite images containing both patterned and unpatterned components result from operating section of the VCSEL array at the same optical power and operating other sections of the VCSEL array with optical powers that vary spatially over the array as shown in FIG. 5C.

Optical patterns produced by the optically based optically-based pattern generator 24 may include, but are not limited to, a set of high resolution optical patterns, binary patterns, gray patterns, phase shift patterns, hybrid gray and phase shift patterns, rainbow patterns, continuously varying color patterns, color coded stripes, wavelength coded stripes, wavelength pattern, segmented stripes, gray scale coded stripes, De Bruijin Sequence, Pseudo Random Binary dots, mini-patterns as codewords, color coded grids, two dimensional coded, two dimensional coded dot array, and/or any combination thereof. Exemplary patterns and associated measurement techniques may be found in the article by Jason Geng, Structured-light 3D Surface Imaging: a tutorial, *Advances in Optics and Photonics* 3, 128-160 (2011), which is hereby incorporated by reference in its entirety.

Figure 6A:
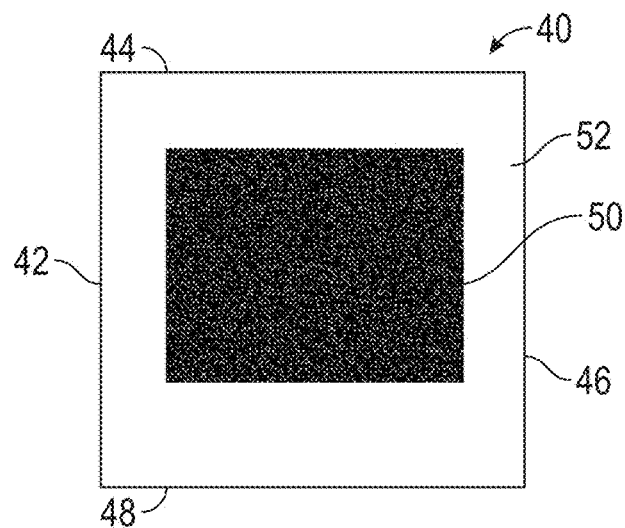
FIGS. 6A-6C illustrate exemplary composite frames provided by an optically-based pattern generator in accordance with the present disclosure.

Referring to FIG. 6A, illustrated therein is composite frame 40 provided by the illuminator 18 having sides 42, 44, 46 and 48. The composite frame 40 consists of at least one section with patterned illumination 50 and at least one section of unpatterned (solid) illumination 52. In one example as illustrated in FIG. 6A, a the patterned illumination 50 is positioned within in a center of the composite frame 40 and unpatterned illumination 52 is positioned about and extending along the sides 42, 44, 46 and 48 as illustrated in FIG. 6A. With regards to the pattern illustrated in FIG. 6A, the patterned illumination may be used for constructing three-dimensional point clouds and the solid illumination may be used for registration and mapping as described in further detail herein. The patterned infrared illumination constitutes 50% of the illuminated area and the solid (unpatterned) illumination constitutes 50% of the illuminated area in FIG. 6A; however, other combinations of the illuminated areas are possible.

Figure 6B:
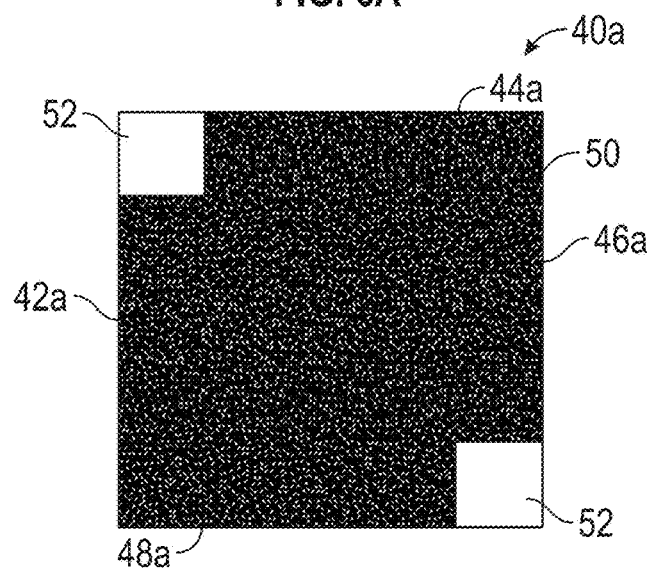
Figure 6C:
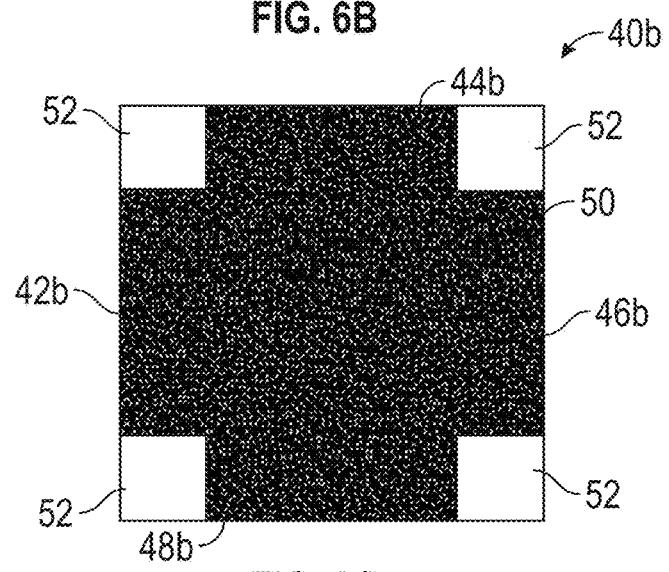

Referring to FIG. 6B, illustrated therein is composite frame 40a having sides 42a, 44a, 46a and 48a. The composite frame 40a consists of at least one section with patterned illumination 50a and at least one section of unpatterned (solid) illumination 52a. In one example, as illustrated in FIG. 6B, a corner area pattern wherein the unpatterned illumination 52a is limited to corners of the frame between sides 42a and 44a, and sides 46a and 48a with the patterned illumination 50a constituting the remaining area of the composite frame 40a. In FIG. 6B, unpatterned illumination 52a comprises just about 8% of the total frame area, contain solid (unpatterned) illumination. In FIG. 6C, where four corners between sides 42b, 44b, 46b and 48b, comprising less than 20% of the total area of the composite frame 40b, contain unpatterned illumination 52b.

The optical scanning system 12 records images of the light beams projected onto the tissue of the colon wall using one or more camera(s) 20, e.g., high-resolutions infrared camera(s). Each recorded image represents one frame captured at a specific time. During the scanning process, the illuminator 18 may illuminate the structure (e.g., area within the colon) with one or more different images or frames (i.e., multi shots such as binary code, gray code, phase shift code, hybrid of gray code and phase shift code, other hybrids, and/or the like), or single image or frame (i.e., single shot such as color coded stripes, wavelength coded stripes, wavelength pattern, segmented stripes, gray scale coded stripes, De Bruijin sequence, pseudo random binary dots, mini-patterns as codewords, color coded grid, two dimensional color coded dot array, hybrids, and/or the like). The illuminator may project a structured-light image, an unpatterned (solid) illumination, or a composite image containing both patterned and unpatterned sections during the capture of each frame.

The camera 20 may possess responsivity to infrared, visible or both visible and infrared light. Additionally, the camera 20 may be configured to produce high-resolution images of the projected pattern and have both length and width dimensions that minimize the dimensions of the optical scanning system 12. In some embodiments, the camera 20 may include a mono sensor with a pixel size between 1 µm and 1.4 µm and an array of 1900×1900 pixels. The pixel size determines the focal length of the optical scanning system 12 in pixels, according to EQ. 1.

$$f_P = \frac{f_{mm}}{p_{mm}} \tag{EQ. 1}$$

wherein $f_p$ is the focal length in pixels, $f_{mm}$ is the focal length of the optical scanning system 12 in millimeters, and $p_{mm}$ is the pixel size in millimeters. In some embodiments, sensor dimensions do not exceed 4.5 mm×3.5 mm to allow sufficient space for the components of the illuminator 18 and to allow for sufficient separation between the camera 20 and the illuminator 18 to achieve sub-millimeter or millimeter accuracy from the triangulation algorithms implemented in the software processing systems as described in further detail herein.

In some embodiments, a camera optics system 29 may be positioned adjacent to the camera 20 to facilitate light collection and/or provide the proper optical geometry for achieving high-accuracy optical scanning. The camera optics system 29 may include, but is not limited to a single optical element, convex lens, meniscus lens, concave lens, or combination of two or more optical elements, convex lens, meniscus lens and/or concave lens. In some embodiments, the camera optics system 29 used with the camera 20 may be substantially similar to or identical to the optical imaging system 28 used with the optical source 27 (e.g., when using a single camera with a single structured light source).

Referring to FIGS. 1, 5A-5C and 6A-6C, in some embodiments, the control system 26 and/or control system 16 synchronizes the optical source 27, optically-based pattern generator 24, and camera 20 to produce and capture illumination patterns 50 and 52 produced by the illuminator 18, varies illumination patterns 50 and 52 between frames 40, and may capture orientation and angular momentum data from the AHRS unit 14. The control system 26 includes, but is not limited to, a source controller 54 and a synchronization subsystem 56.

The source controller 54 ensures that the correct drive current(s) are provided to the optical source 27 during each frame 40 captured by the optical scanning system 12. For example, for a single laser diode or a static VCSEL array source as illustrated in FIG. 4, the source controller 54 maintains a desired level of current to the laser diode or to each VCSEL in the array. For the embodiment in which the source output alternates between patterned illumination and unpatterned (solid) illumination, for example for the source depicted in FIGS. 5A-5C, the source controller 54 may select the correct set of drive currents for the corresponding set of VCSELs in the array to produce the desired illumination from the optical source 27. The source controller 54 may include, but is not limited to, a microprocessor, electronic drive circuitry for precise control of current delivered to the source, and digital logic or switches for switching between two or more illumination patterns.

The synchronization subsystem 56 ensures that camera 20 captures an image only after the desired illumination pattern 50 and/or 52 is produced by the illuminator 18. The synchronization subsystem 56 also provides timing signals to the AHRS unit 14 to ensure that orientation and angular momentum data is captured at the exact same time as the capture of the image by the camera 20. The synchronization subsystem 56 may include, but is not limited to, a microprocessor and a timing signal generation system.

The geometrical arrangement of the illuminator 18 and/or camera 20 may determine design of size and resolution of the optical scanning system 12. Further, resolution impacting the measurement accuracy achieved after the processing software produces the 3D point cloud may be affected by geometrical arrangement of the illuminator 18 and/or camera 20. Described herein are exemplary parallel configurations and exemplary converged configurations; however, descriptions of each are not to be considered limiting as other configurations may be contemplated by one skilled in the art and within the bounds of teachings within the description (e.g., configurations that alter size, resolution of the optical scanning system and configurations that impact measurement accuracy).

Figure 7A:
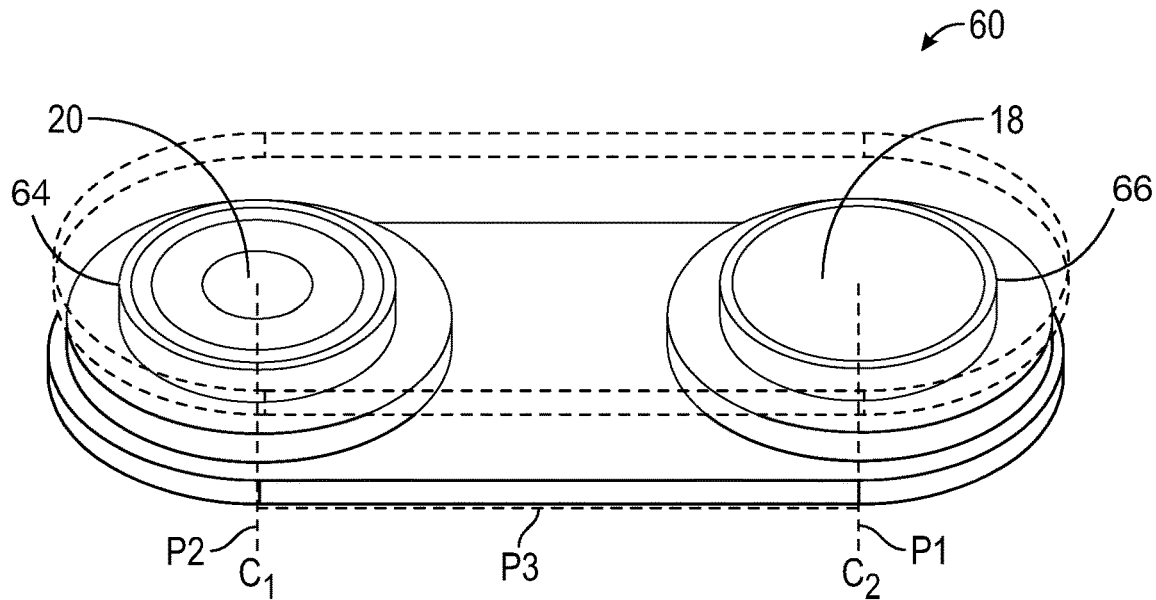
FIG. 7A is a perspective view of an exemplary embodiment of an optical scanning system having a parallel configuration of an optical source and a camera.
Figure 7B:
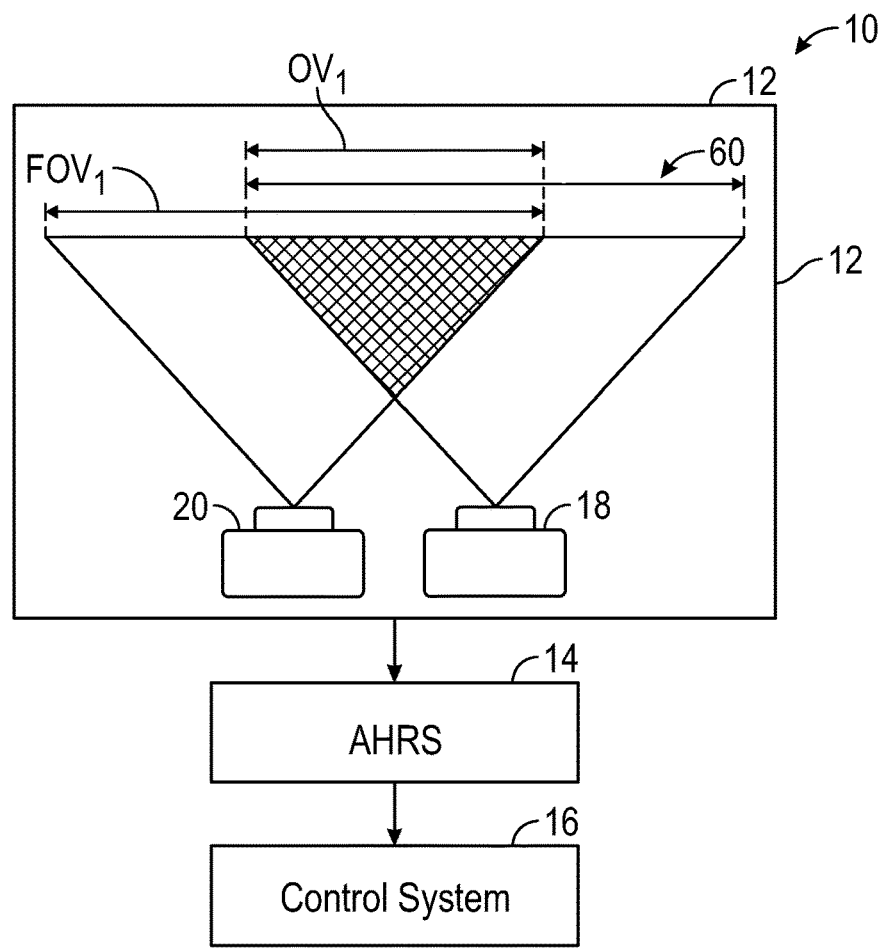
FIG. 7B is a block diagram of an exemplary embodiment of a colonoscopy system having the optical scanning system of FIG. 7A.

FIGS. 7A and 7B illustrate an exemplary optical scanning system 12 having a parallel configuration 60 of the illuminator 18 and the camera 20 wherein the illuminator 18 and the camera 20 are along a plane $P_1$ and have an orientation perpendicular to the surface of the plane $P_1$. For example, the illuminator 18 is oriented in the direction of plane $P_3$ with plane $P_3$ positioned perpendicular to plane $P_1$. Similarly, the camera 20 is oriented in the direction of plane $P_2$, with the plane $P_2$ positioned perpendicular to plane $P_1$. Referring to FIG. 7B, for the parallel configuration 60, an overlap area $OV_1$ of tissue is illuminated by the illuminator 18 within the field of view $FOV_1$ of the camera 20. In some embodiments, the illuminator 18 illuminates an area of tissue within as much of the $FOV_1$ of the camera 20 as possible. Increasing the overlap area $OV_1$ reduces the minimum depth from which the optical scanning system 12 can obtain data about the illuminated tissue of the wall of the colon.

For the camera 20, the $FOV_1$ is determined by sensor dimensions and focal length of the camera optics system 29 placed in front of the camera 20. The $FOV_1$ depends on the angle of view ($\alpha$), defined as the angle over which the sensor can collect light from the scene. The angle of view, in radians, is given by:

$$\alpha = 2 * \tan\left(\frac{W(s - f_{mm})}{2sf_{mm}}\right) \qquad (EQ.\ 2)$$

wherein W is the width of the sensor used in the camera 20, s is the distance between the subject (e.g., wall tissue of the colon) and the sensor, and $f_{mm}$ is the focal length of the camera optics system 29. The $FOV_1$ depends on the angle of view (AOV) according to:

$$FOV_1 = 2 * \tan\left(\frac{\alpha}{2}\right) * d \qquad (EQ.\ 3)$$

wherein d is the distance (or depth) to the tissue from the camera 20.

The parallel configuration 60 shown in FIG. 7A may additionally be influenced by measurements of baseline L and end-to-end length EE. Baseline L is defined as distance between center $C_1$ of the camera 20 and center $C_2$ of the illuminator 18. The end-to-end length EE is defined as distance between an outer edge 64 of the camera 20 and an outer edge 66 of the illuminator 18. In some embodiments, the end-to-end length EE may be limited to less than approximately 12 mm. Accuracy in depth $d_a$ depends on the operating distance h between the optical scanning system 12 and the tissue under investigation, the focal length f of the optical imaging system 28, and the distance of the baseline L according to the formula:

$$d_a = \frac{h^2}{Lf} c_e \qquad (EQ.\ 4)$$

wherein $c_e$ is a calibration and matching error correction factor (in pixels) in the processing software. As an example, if the camera 20 possesses 1920×1080 pixels with pixel dimension of 1.4 µm, combined with the optical scanning system 12 having f=1.83 mm, a baseline L=4 mm, and package dimensions of 4.1 mm×3.9 mm produces a depth accuracy of 1.5 mm at a nominal h=2.5 cm and allows an end-to-end length EE of 8 mm. The accuracy in the lateral direction ($e_l$) is determined by:

$$e_l = \frac{h}{f_p} e_a \qquad (EQ.\ 5)$$

wherein $f_p$ is the focal length in pixels, and $e_a$ is the algorithm error in pixels, and is typically fixed at 0.5 times the pixel mean error.

Figure 8A:
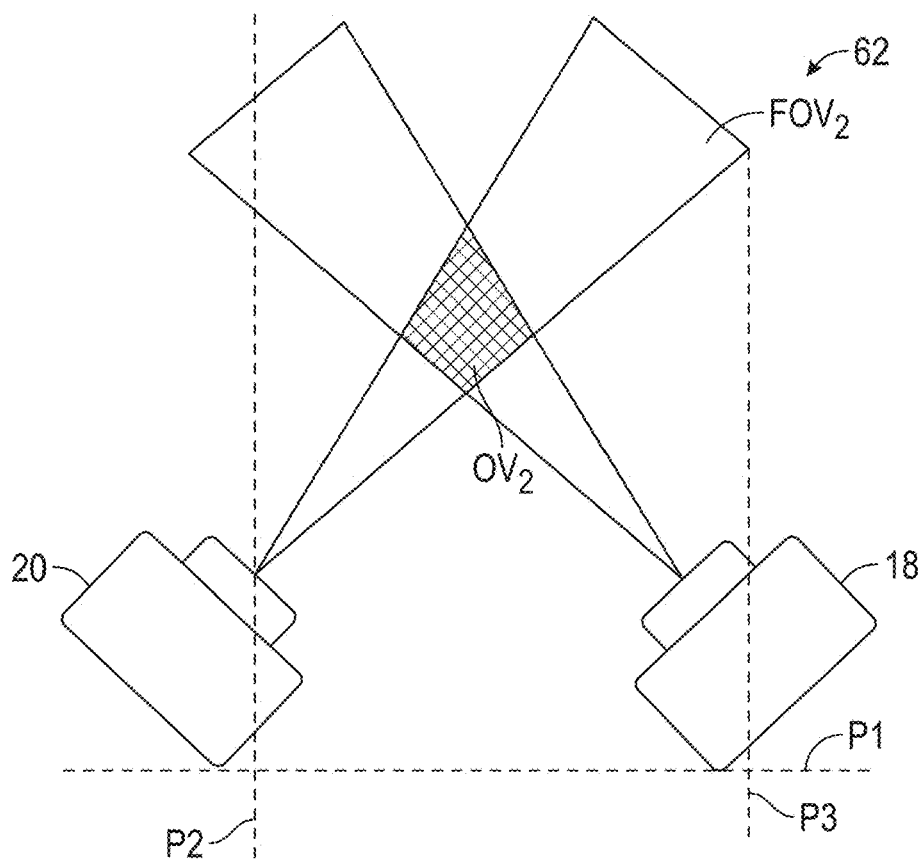
FIGS. 8A and 8B are block diagrams of exemplary optical scanning systems having converged configurations of an optical source and camera.
Figure 8B:
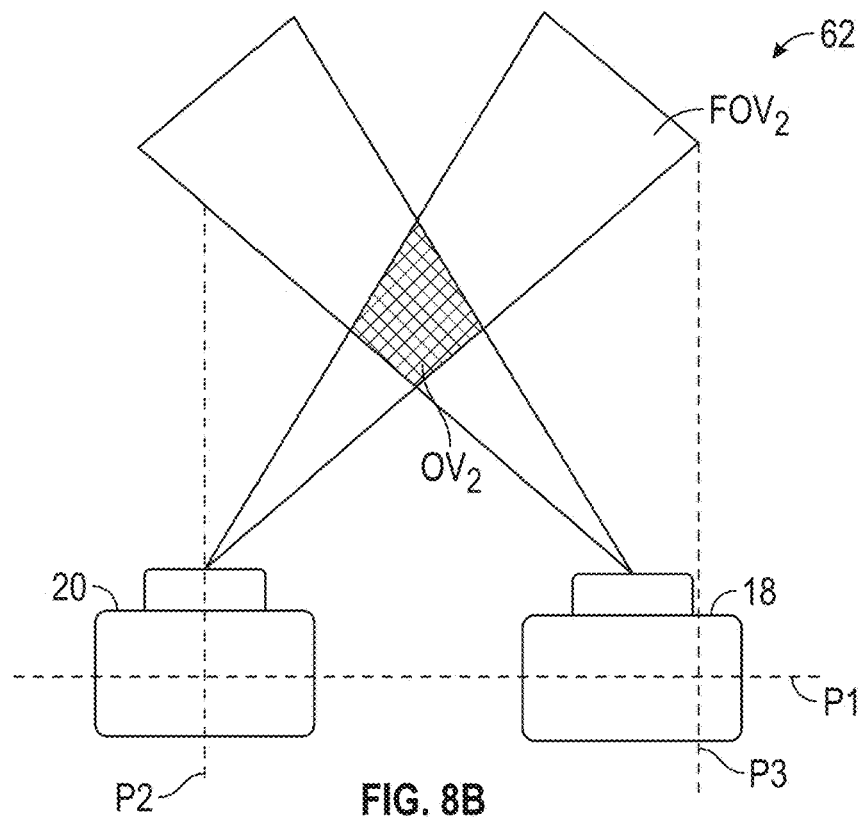

FIGS. 8A and 8B illustrate an exemplary converged configuration 62 of the illuminator 18 and the camera 20 wherein the illuminator 18 and/or the camera 20 are each tilted at an angle about the planes $P_2$ and $P_3$ respectively. In some embodiments, only one of the camera 20 or the illuminator 18 may be tilted about the plane $P_2$ and $P_3$ respectively. Converged configurations 62 may include, but are not limited to, (a) physically tilting the camera 20 and the illuminator 18 toward each other at some angle (hardware tilting as shown in FIG. 8A), or (b) designing the optical imaging system 28 to tilt the FOV and the projected beam toward each other, with the camera 20 and the illuminator 18 remaining physically parallel to each other (optical tilting as shown in FIG. 8B).

Figure 9A:
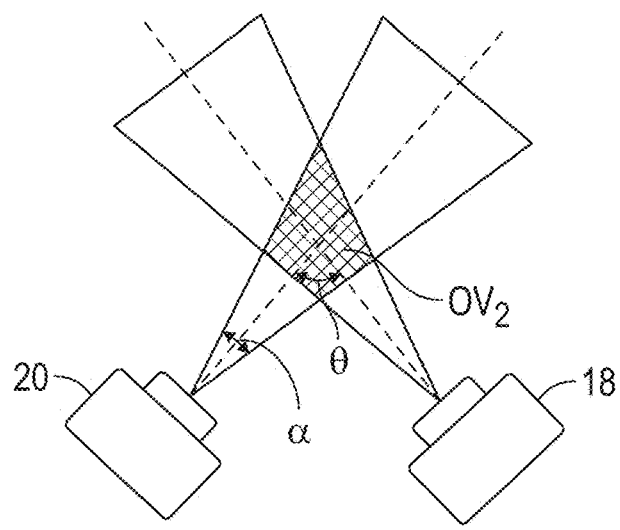
FIGS. 9A-9C are block diagrams of exemplary optical scanning systems having converged configurations resulting in different overlap areas.
Figure 9B:
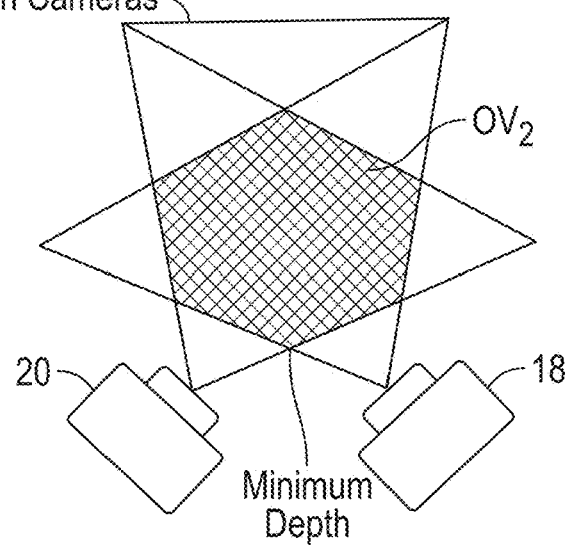

For the converged configuration 62, the tilting angle and the AOV determine an overlap area $OV_2$. If the tilting angle is less than the AOV, the overlap area $OV_2$ possesses a minimum depth from which the camera 20 can collect image data, as shown in FIG. 9A. FIGS. 9A and 9B illustrate instances wherein the tilting angle is respectively greater than and less than the AOV. As shown, the overlap area $OV_2$ possesses both a minimum and a maximum depth from which the camera 20 can collect image data, as shown in FIG. 9B. For a given AOV and baseline distance, the minimum depth achieved by the converged configuration 62 may be less than the minimum depth achieved by the parallel configuration 60. The AOV and FOV of the camera 20, the depth accuracy, and the lateral accuracy may be determined using EQ. 2-5 described herein.

FIGS. 10-19 illustrate exemplary embodiments of the colonoscopy systems 10 in accordance with the present disclosure.

Figure 10:
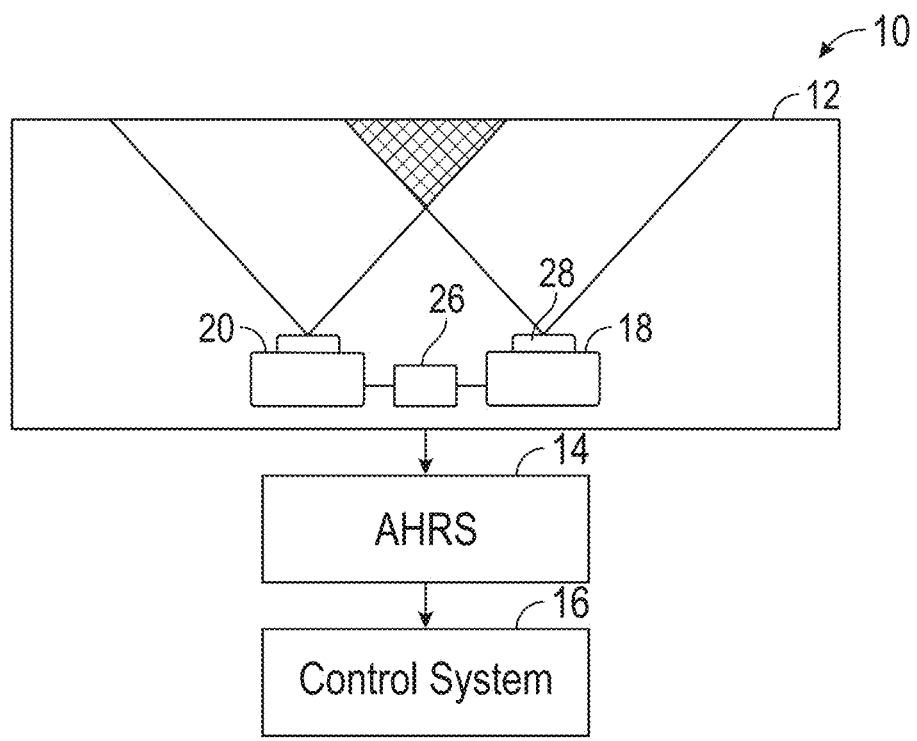
FIG. 10 is a block diagram of an exemplary colonoscopy system having at least one camera and at least one structure optical source in accordance with the present disclosure.

FIG. 10 illustrates an exemplary colonoscopy system 10 with one camera 20 and at least one structured illuminator 18. The camera 20 may be a high-resolution camera sensitive to infrared light and configured to record at least one image of light projected onto a surface of tissue under investigation. Additionally, the colonoscopy system 10 may include at least one optical imaging system 28 that imposes a spatial intensity and/or wavelength variation on light from at least one illuminator 18, and the electronic control system 26 configured to synchronize one or more optical sources 27, the optically-based pattern generator 24, and the camera 20. As described in further detail here, properties, arrangement and/or configuration of the illuminator 18, optically-based pattern generator 24, camera 20 and/or the like within the colonoscopy system 10a and further within mechanical housing encasing the components (e.g., ring about the endoscopic instrument 22, internal to the endoscopic instrument 22 as shown in FIGS. 2A, 2B and 3) may determine performance of the colonoscopy system 10 in terms of lateral and depth resolution, depth of tissue for which the target resolution is achieved, and the field of view over which the system can make measurements.

The control system 26 may be configured to synchronize the optical source 27, optically based pattern generator 24, and camera 20 to produce and capture illumination patterns produced by the illuminator 18, vary illumination patterns between frames 40 (shown in FIGS. 5-6), and capture orientation and angular momentum data from the AHRS unit 14.

The control system 16 may associate components of the pattern recorded in the image obtained by the camera 20 with the corresponding point(s) in the original projected pattern, and measure the translation and rotation of the optical scanning system 12 between successive frames. Using the data, the control system 16 may construct one or more three-dimensional point clouds and perform registration calculation to stitch the 3D point clouds into a mapping of the tissue illuminated by the illuminator 18. Outputs of the control system 16 may include, but are not limited to, alert, detection and/or identification of polyps and adenomas, measurements of height and circumference of the polyps and adenomas, measurement data and other informational icons for augmented displays, three-dimensional models of the scanned areas or lengths of the colon, and control signals for semi-autonomous and autonomous operation of the endoscopic system 22.

Referring to FIGS. 5A-5C, 6A-6C and 10, the exemplary colonoscopy system 10, the illuminator 18 illuminates tissue in the walls of the colon with structured light. In this context, structured light consists of light with regular and controlled spatial variation in intensity, typically referred to as spatial patterns. Such optical patterns may include, but are not limited to, a set of high resolution optical patterns, binary patterns, gray patterns, phase shift patterns, hybrid gray and phase shift patterns, rainbow patterns, continuously varying color patterns, color coded stripes, segmented stripes, gray scale coded stripes, De Bruijin Sequence, Pseudo Random Binary dots, mini-patterns as codewords, color coded grids, two dimensional coded dot array, and/or any combination thereof. Exemplary patterns and associated measurement techniques may be found in the article by Jason Geng, Structured-light 3D Surface Imaging: a tutorial, Advances in Optics and Photonics 3, 128-160 (2011), which is hereby incorporated by reference in its entirety. The structured light of the illuminator 18 may further consist of combinations of an area containing one of the potential patterned illumination 50 with one or more areas containing unpatterned illumination 52 (i.e., solid illumination), as shown in FIGS. 5A-5C and FIGS. 6A-6C.

During the scanning process, the illuminator 18 may illuminate with one or more different images or frames 40 (i.e., multi shots such as binary code, gray code, phase shift code, hybrid of gray code and phase shift code, other hybrids, and/or the like), or single image or frame 40 (i.e., single shot such as color coded stripes, segmented stripes, gray scale coded stripes, De Bruijin sequence, pseudo random binary dots, mini-patterns as codewords, color coded grid, two dimensional color coded dot array, hybrids, and/or the like). For some embodiments, the illuminator 18 may alternate between illumination of the colon wall, for example, with patterned illumination 50 and unpatterned illumination 52, with the alternation occurring between successive frames 40 and/or time intervals. The camera 20 may be a single, high-resolution camera configured to capture one or more images of the colon tissue, for example, illuminated by the illuminator 18, with the image showing the projection of the patterned illumination 50 and/or unpatterned illumination 52 onto the three-dimensional space.

For frames 40 that include patterned illumination 50 or patterned components of composite frames 40, a matching operation may be performed, wherein each part of the projected pattern is matched to a component of the original pattern stored in memory. As such, a determination may be made on which portion of the original pattern illuminated each section of tissue within the colon. Matching data, along data related to geometrical arrangement of the camera 20 and the illuminator, may be input into sophisticated triangulation algorithms. The triangulation algorithms use the information to calculate a location in 3D space for each segment of the colon tissue. Repeating the process for two different patterns projected on the same section of tissue increases the accuracy of the triangulation process and allows the colonoscopy system 10 to produce highly accurate three dimensional point cloud representation of the illuminated tissue.

For the frames 40 having unpatterned illumination 52 or unpatterned components of composite frames 40, a matching operation may be performed between the patterns of blood vessels contained in each frame 40, wherein specific features or patterns of blood vessels are matched between successive frames by global or semi-global registration techniques. Blood vessel matching information may be used in addition to the 3D point clouds from the patterned frames, and the orientation and angular velocity data collected from the AHRS unit 14 at every frame, to perform registration between the 3D point clouds and subsequently construct a 3D model of the colon wall.

Figure 11:
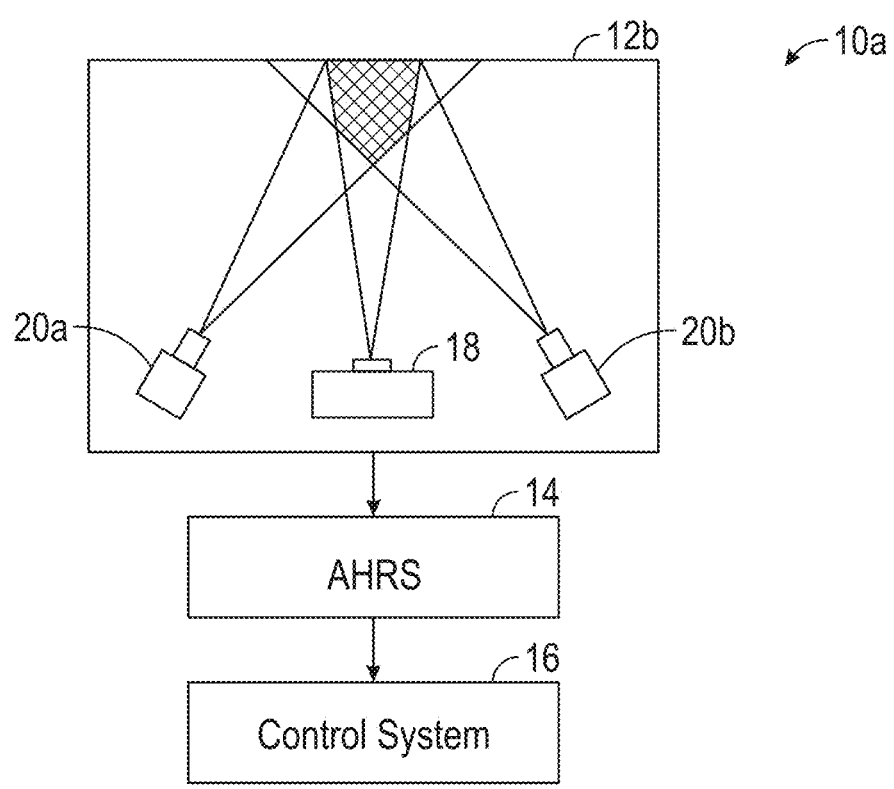
FIGS. 11-14, 15A and 15B illustrate exemplary embodiments of colonoscopy systems having at least one optical source and at least two cameras located at two different positions with respect to the optical source.
Figure 12:
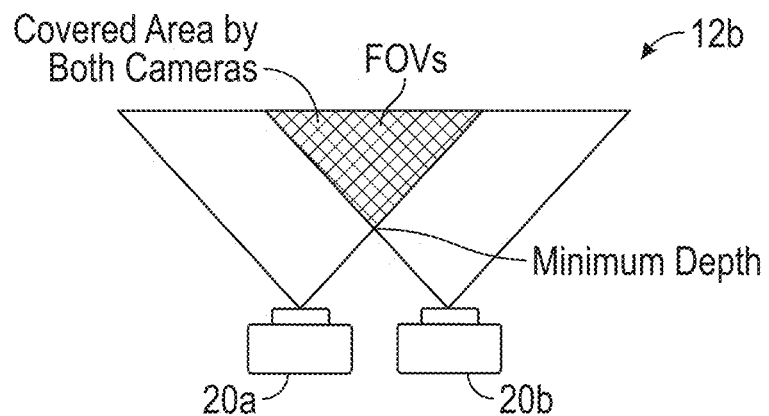
Figure 13:
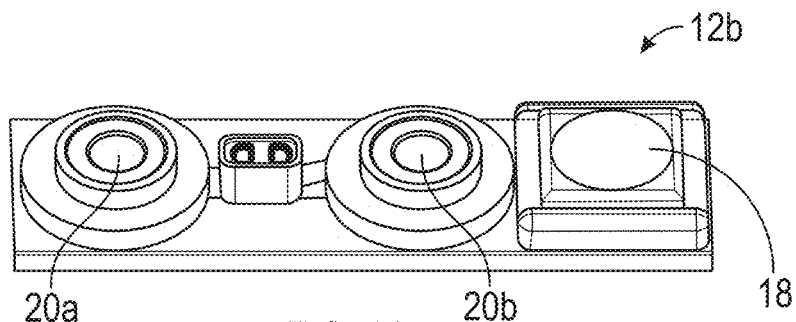

FIGS. 11-13 illustrate exemplary embodiments of the colonoscopy system 10b that include the illuminator 18 and two cameras 20a and 20b located at two different positions with respect to the illuminator 18. The geometrical arrangement of the illuminator 18 and the cameras 20a and 20b determines size and resolution of the optical scanning system 12b. Resolution may impact measurement accuracy achieved after the processing software produces the three dimensional point cloud. Generally, the cameras 20a and 20b are positioned at either end of the optical scanning system 12b, and the illuminator 18 is placed in close proximity to the cameras 20a and 20b, with the illuminator 18 positioned along the same plane to minimize size of the optical scanning system 12b as illustrated in FIG. 11. This configuration between the illuminator 18 and two cameras 20a and 20b is herein referred to as "stereo configuration". FIG. 12 illustrates another implementation of "stereo configuration" wherein the illuminator 18 is positioned between the cameras 20a and 20b. In FIG. 12, the illuminator 18 is positioned at a side of the cameras 20a and 20b.

Generally, the control system 16 performs pattern matching and stereo triangulation between the two cameras 20a and 20b. Additionally, translation and rotation of the optical scanning system 12b is measured between successive frames to construct three-dimensional point clouds from the patterned illumination data. Additionally, registration calculation is performed to the stitch the three-dimensional point clouds into a mapping of the tissue illuminated by the illuminator 18. Outputs may include, but are not limited to, alert, detection and/or identification of polyps and adenomas, measurements of height and circumference of the polyps and adenomas, measurement data and other informational icons for augmented displays, three dimensional models of the scanned areas or lengths of the colon, and control signals for semi-autonomous and autonomous operation of the endoscopic system.

Figure 9C:
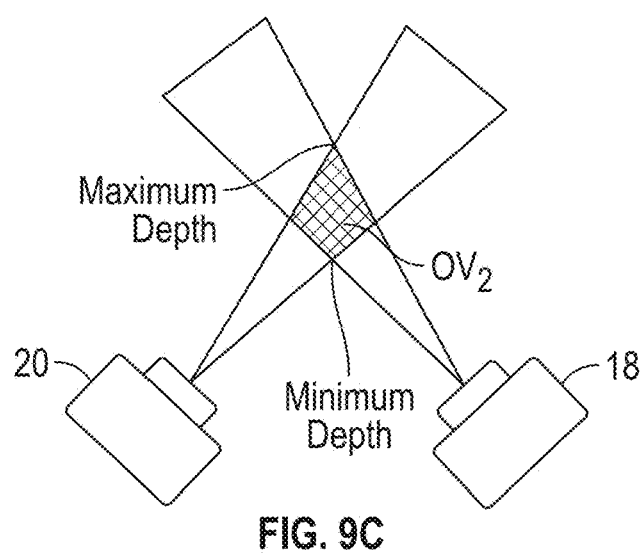

The geometrical arrangement of the optical scanning system 12b may include, but is not limited to a parallel configuration and a converged configuration as described in further detail in FIGS. 7-9 herein. The geometric arrangement of the two cameras 20a and 20b may be such that the illuminator 18 produces a structured light beam that illuminates as much of the combined $FOV_3$ of the cameras 20a and 20b as possible to maximize the area of illuminated tissue recorded.

Figure 14:
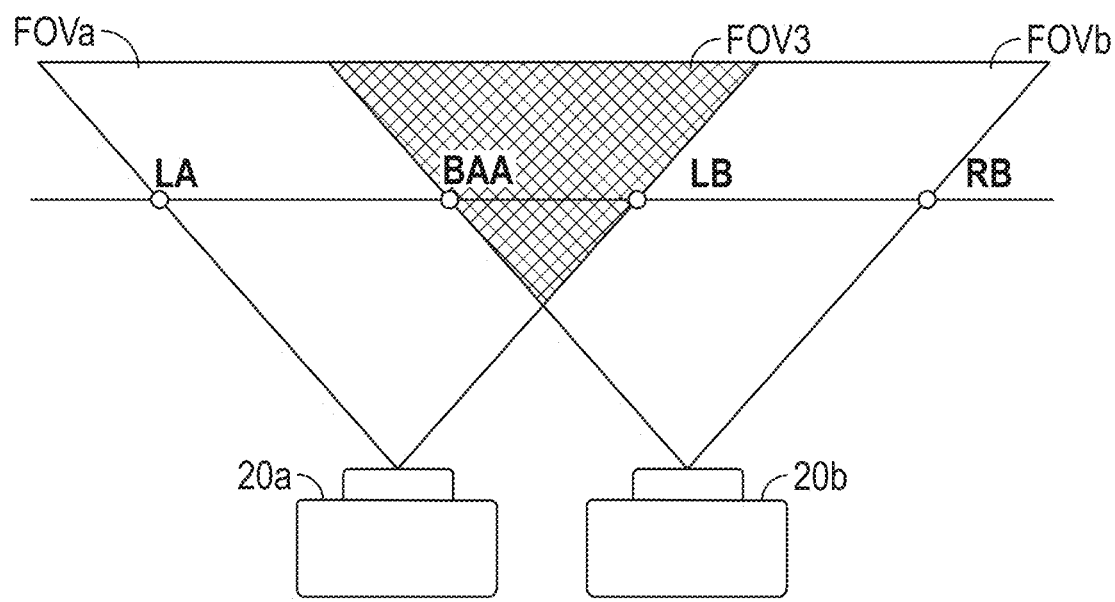
Figures 15A, 15B:
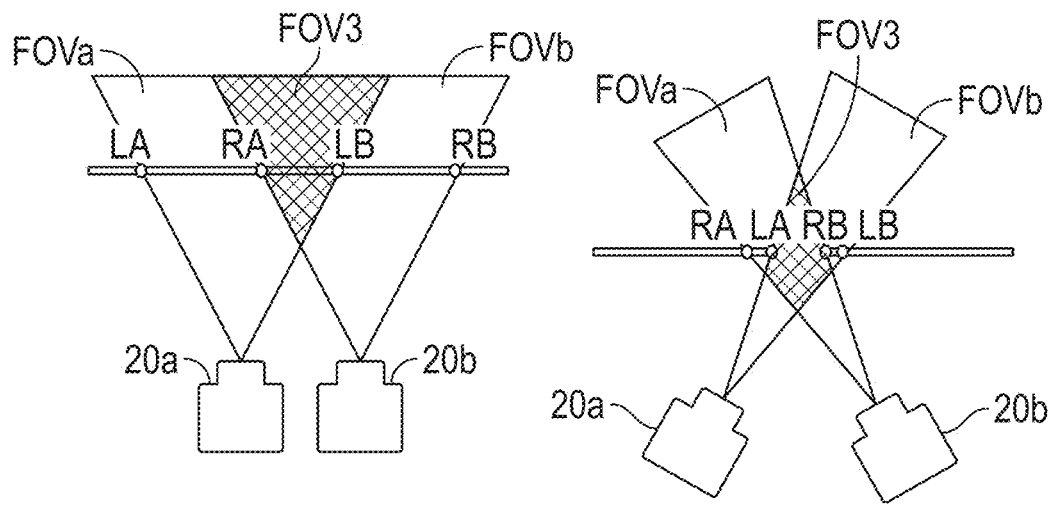

Referring to FIGS. 12 and 13, geometric design of the optical scanning system 12 may consider total stereo $FOV_3$, defined as the mutual FOV the cameras 20a and 20b or the overlap between the individual camera FOVs, as an additional parameter. Computing the mutual $FOV_3$ at a given depth requires four data points, as shown in FIG. 14. The four points are (1) LA, the left most point of the $FOV_a$ of the camera 20a at a chosen depth; (2) LB, the right most point of $FOV_a$ of the camera 20a at a chosen depth; (3) RA, the left most point of the $FOV_b$ of the camera 20b at a chosen depth; and (4) RB, the right most point of the $FOV_b$ of the camera 20b at a chosen depth. Such points may be determined via EQS. 6-9:

$$LA = \tan\left(\frac{-\alpha + \theta}{2}\right) \cdot d \quad \text{(EQ. 6)}$$

$$LB = \tan\left(\frac{\alpha + \theta}{2}\right) \cdot d \quad \text{(EQ. 7)}$$

$$RA = \tan\left(\frac{-\alpha - \theta}{2}\right) \cdot d + b \quad \text{(EQ. 8)}$$

$$RB = \tan\left(\frac{\alpha - \theta}{2}\right) \cdot d + b \quad \text{(EQ. 9)}$$

wherein $\alpha$ is the FOV, $\theta$ is the stereo tilt angle, d is the depth in millimeters and b is the baseline between the cameras 20a and 20b in millimeters. The mutual or stereo $FOV_3$ can be calculated for the two cases shown in FIGS. 15A and 15B. For FIG. 15A, the stereo $FOV_3$ equals LB–RA. For FIG. 15B, the stereo $FOV_3$ equals RB–LA.

Figure 16A:
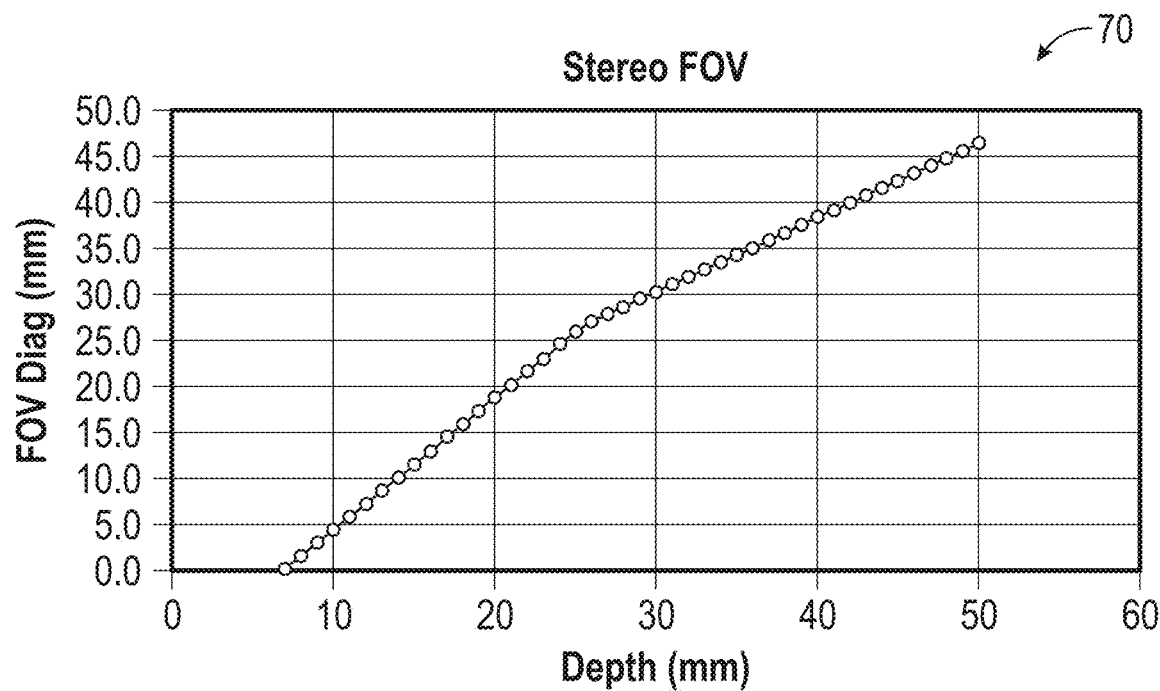
FIGS. 16A-16C are graphs illustrating dependence of field of view, depth error and lateral error on depth between cameras and tissue wall of a colon.
Figure 16B:
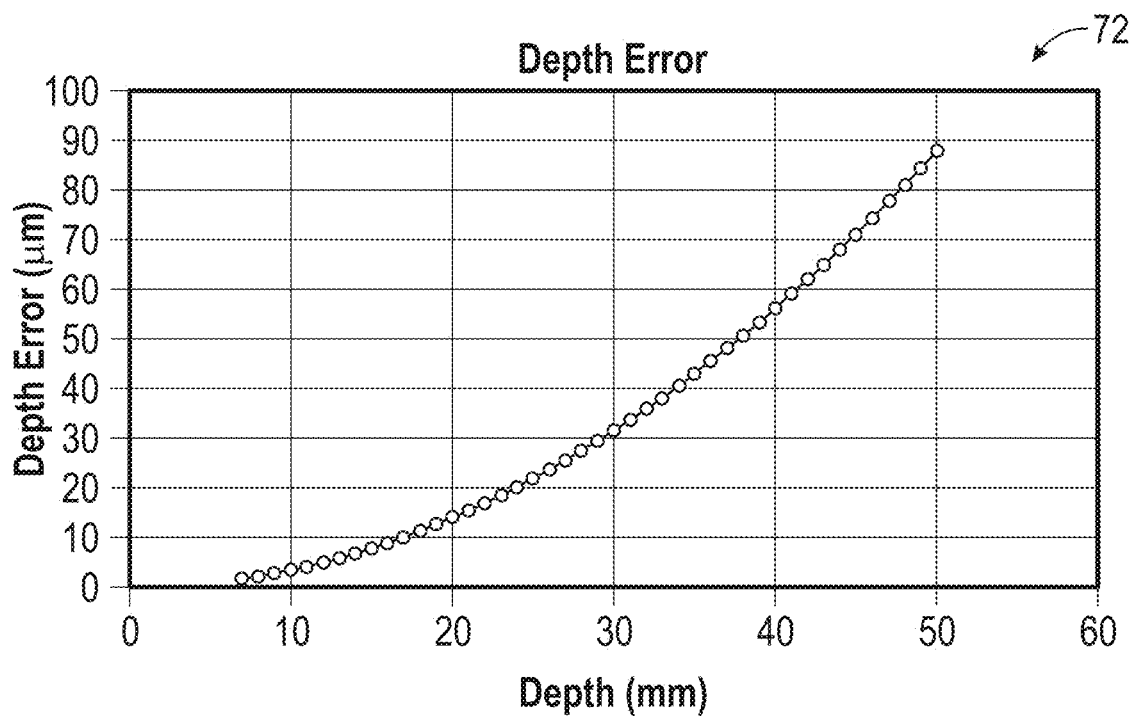
Figure 16C:
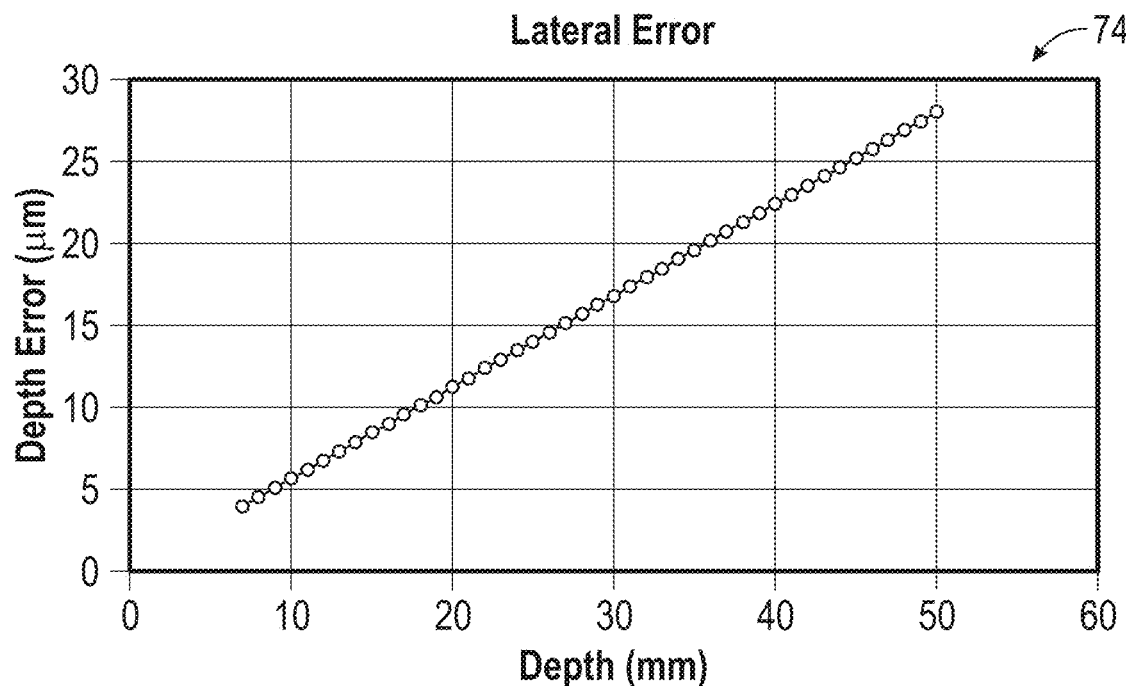

Referring to FIGS. 16A-16C, in one example, an OV02281-GA4A sensor is used in the camera 20a, which has a pixel size of 1.12 µm, an array size of 2.214×2.214 mm, and a package size of 4050×3400.2 µm. The optical scanning system 12b has a focal length of 2 mm with the cameras 20a and 20b. The optical scanning system 12b also includes a baseline of 7.95 mm and stereo tilt angle of 14° between the cameras 20a and 20b. At a depth of 25 mm, the resultant stereo $FOV_3$ width is 26 mm, over 99.5% of the FOV is used in capturing the image projected by the illuminator 18, the depth error is 22 µm, the lateral error is 14 µm, and the cameras 20a and 20b can capture images for all depths beyond 6.8 mm (i.e., the depth range is 6.8 mm to infinity). FIGS. 16A, 16B and 16C are graphs 70, 72 and 74, respectively, that show the dependence of the $FOV_3$, depth error, and lateral error on the depth, respectively, between the cameras 20a and 20b and the tissue wall of the colon.

Referring to FIGS. 5-6 and 11-12, for the patterned frames or patterned components of composite frames 40, a matching operation may be performed wherein a determination is made as to the position of the same component of the projected pattern within both of the captured images, using the original pattern stored in memory. Location of each pattern component in the two images may be used and information on the geometry between the two cameras 20a and 20b may be input into the triangulation algorithms. The triangulation algorithms use the information to calculate a location in three-dimensional space for each segment of the colon tissue, and subsequently produce a highly accurate three-dimensional point cloud representation of the illuminated colon tissue.

For the unpatterned (solid) frames or unpatterned components of composite frames 40, a matching operation may be performed between the patterns of blood vessels in each frame 40, using data from the images captured by both cameras 20a and 20b. Specific features or patterns of blood vessels are matched between successive frames 40 by global or semi-global registration techniques. Blood vessel matching information, the three-dimensional point clouds from the patterned frames 40, and the orientation and angular velocity data collected from the AHRS unit 14 at every frame, may be used to perform registration between the three-dimensional point clouds and subsequently construct a three-dimensional model of the colon wall.

Figure 17:
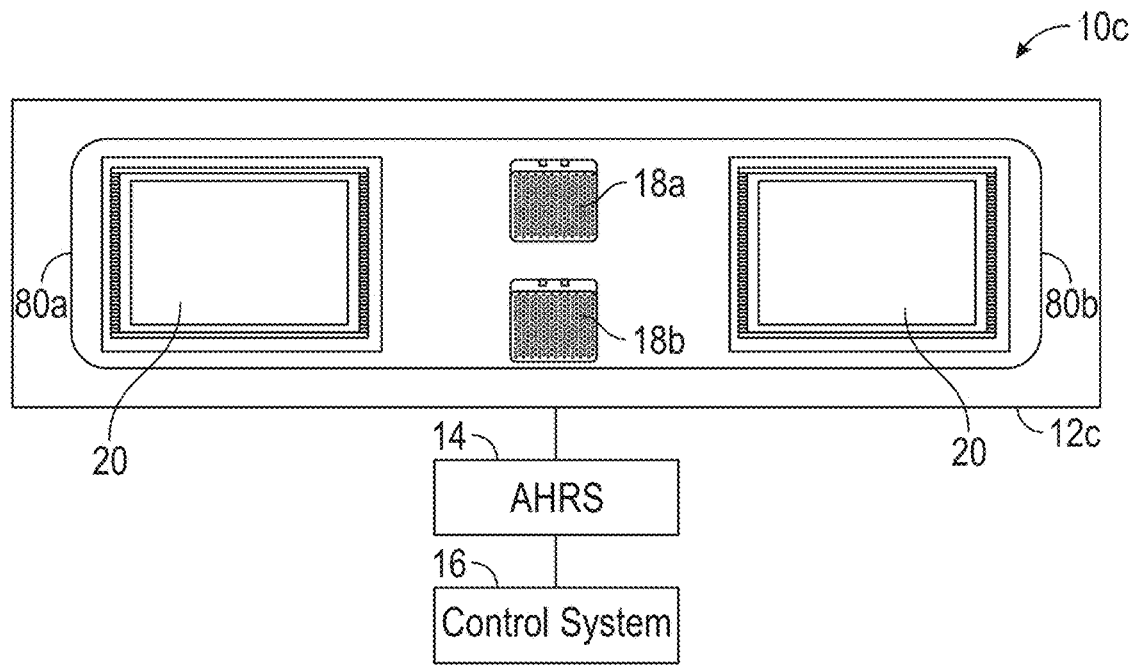
FIG. 17 is a block diagram of an exemplary colonoscopy system having two optical sources and at least one camera.

FIG. 17 illustrates an exemplary embodiment of the colonoscopy system 10c that includes two illuminators 18a and 18b, and at least one camera 20 to produce image data for processing by the control system 16. The illuminators 18a and 18b may be comprised of a structured light source and a solid light source (i.e., flood source) as defined herein.

Generally, the colonoscopy system 10c includes, but is not limited to, subsystem one which now consists of the two illuminators 18a and 18b having one or more optically-based pattern generators 24 applied to at least one optical source 27a and/or 27b, at least one camera 20 (e.g., high resolution camera), and at least one control system 26. The properties of the components within the illuminators 18a and 18b and the camera 20, the arrangement of the with respect to each other and/or the configuration of the optical scanning system 12c within housing encasing the components on or within the endoscopic system 22 may determine the performance of the colonoscopy system 10c in terms of lateral and depth resolution, the depth of tissue for which the target resolution is achieved, and the field of view over which the colonoscopy system 10c can make measurements.

At least one of the components of the illuminator 18a or 18b (e.g., infrared light source), may be separate from the other illuminator 18a or 18b (e.g., structured light source), and illuminate the tissue under investigation with a solid or uniform intensity. In some embodiments, the illuminator 18a or 18b having the structured light source and the illuminator 18a and 18b providing solid illumination may illuminate the tissue in alternating frames 40, with one of the illuminators 18a or 18b providing illumination and the other illuminator 18a or 18b turned off in one frame 40, and the alternate illuminator 18a or 18b turned on. In some embodiments, both of the illuminators 18a and 18b may illuminate the tissue in one frame 40, with the illuminator 18a or 18b providing solid illumination illuminating the tissue in the subsequent frame 40.

The geometrical arrangement of the illuminators 18a and 18b, and the camera(s) 20 may determine the size and resolution of the optical scanning system 12c, with the resolution impacting the measurement accuracy achieved after the processing software produces the three-dimensional point cloud. Referring to FIG. 17, the camera(s) 20 may be positioned at either end 80a and 80b of the optical scanning system 12c. At least one illuminator 18a or 18b (i.e., providing structured light) may be positioned in close proximity to the camera(s) 20. The illuminator 18a or 18b providing solid illumination may be positioned between the cameras 20 and next to the illuminator 18a or 18b providing structured light, outside the cameras 20, or outside the baseline between the camera(s) 20 and the illuminator 18a or 18b providing structured light, for example, in an orthogonal direction to the that of the baseline. Other positioning is herein contemplated. FIG. 17 illustrates an exemplary embodiment with the illuminator 18a providing structured light and the illuminator 18b providing solid (i.e., flood) illumination positioned between two cameras 20 along the same plane to minimize the size of the optical scanning system 12c.

The geometrical arrangement of the optical scanning system 12c may include, but is not limited to a parallel configuration and a converged configuration as described previously herein. In both the parallel configuration and converged configuration, the geometric arrangement of the two cameras 20 may be the primary concern. The illuminator 18a or 18b providing structured light is configured to produce a structured light beam that illuminates as much of the combined FOV of the cameras 20 as possible to maximize the area of illuminated tissue recorded. The illuminator 18a or 18b providing solid (flood) light is also configured to produce a constant or nearly constant illumination intensity that illuminates as much of the combined FOV of the cameras 20 as possible to maximize the ability of the system to accurately perform registration operations. In some embodiments, the illuminator 18a or 18b providing solid (flood) light may illuminate an area larger than the combined FOV to provide sufficient data to produce accurate registration.

Referring to FIGS. 1, 4A-4B, and 17, the illuminator 18a or 18b includes the optical imaging system 28 and optical source 27. The optical imaging system 28 collects the light from the optical source 27 and controls the divergence of the optical beam for each illuminator 18a and 18b. The optical imaging system 28 used for the illuminator 18a or 18b providing structured light may be different in components, structure, and performance parameters than the illuminator 18a or 18b providing solid illumination. The optical imaging system 28 may include, but is not limited to, a single convex lens or a combination of two or more convex and/or concave lenses. For the structured light source, the design of the optical imaging system 28 may be selected such that the focal length of the optical imaging system 28 may produce a primary imaging point at the average distance between the optical scanning system 12c and the colon wall, typically around 3 cm, and may produce a long depth of focus, (e.g., extending between 1 cm and 5 cm), to allow projection of sharp, high-contrast images for a range of distances between the optical scanning system 12c and the colon wall. Exemplary focal lengths for use may be configured to minimize the distance between the illuminator 18a or 18b and the optical imaging system 28 to minimize the size (in depth) of the optical scanning system 12c to facilitate integration with or mounting on the endoscope 22. For the illuminator 18a or 18b providing solid illumination, the design may be configured to project a constant or nearly-constant illumination over the tissue that falls within the field of view (FOV) of the camera(s) 20, in order to provide sufficient detail to maximize the performance of the mapping, registration and modeling software system, for example.

The illuminator 18a or 18b providing structured light projects patterns onto the colon wall, wherein the patterns may consist of, but are not limited to, arrays of dots, lines, and other geometric figures, and may or may not also contain color variations. The illuminator 18a or 18b providing solid (unpatterned) light illuminates the colon wall with a uniform illumination. The two illuminators 18a and 18b illuminate the colon wall in alternating frames or time intervals. One or two cameras 20 capture an image of the colon tissue illuminated by the illuminator 18a or 18b providing structured light or the illuminator 18a or 18b providing solid (unpatterned) light, with the image showing the projection of the optical pattern or solid illumination onto the three-dimensional space.

For the patterned frames 40, the software first performs a matching operation, wherein each part of the projected pattern is matched to a component of the original pattern stored in memory. In this way, the software determines which part of the original pattern illuminated each section of tissue within the colon.

Specialized analysis software employs triangulation algorithms to associate components of the structured-light pattern recorded in the image of the camera 20 with the corresponding point in the original projected pattern and constructs three-dimensional point clouds of the tissue illuminated by the illuminator 18a or 18b providing structured light. To that end, the software uses the matching information, along with information about the geometrical arrangement of the camera 20 and illuminator 18a and/or 18b, as input to sophisticated triangulation algorithms. The triangulation algorithms use the information to calculate a location in three dimensional space for each segment of the colon tissue. Repeating the process for two different patterns projected on the same section of tissue increases the accuracy of the triangulation process and allows the system to produce highly accurate three-dimensional point cloud representation of the illuminated tissue.

The software uses the blood vessel matching information, the three dimensional point clouds from the patterned frames 40, and the orientation and angular velocity data collected from the AHRS unit 14 at every frame 40, to perform registration between the three dimensional point clouds and subsequently construct a three dimensional model of the colon wall. To that end, for the unpatterned (solid) frames 40, the software performs a matching operation between the patterns of blood vessels contained in each frame 40, where specific features or patterns of blood vessels are matched between successive frames by global or semi-global registration techniques. The software further employs algorithms for matching the patterns of blood vessels recorded by the camera 20 in successive frames in response to the illuminator 18a or 18b providing solid illumination, performs registration and stitches together the three-dimensional point clouds to produce three dimensional mappings of the tissue illuminated by the illuminator 18a or 18b. Additional algorithms utilize the three-dimensional point clouds and three dimensional mapping to produce outputs that include, but are not limited to, detection and identification of polyps and adenomas, measurements of height and circumference of the polyps and adenomas, measurement data and other informational icons for augmented displays, and control signals for semi-autonomous and autonomous operation of the endoscopic system 22.

Figure 18:
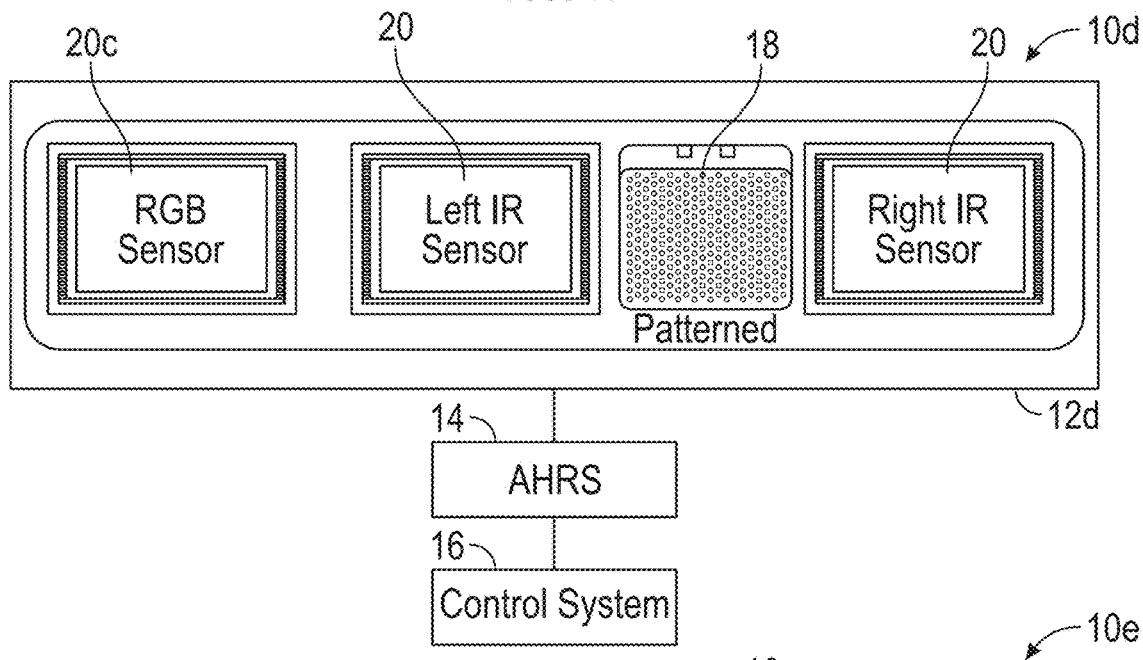
FIGS. 18 and 19 illustrate exemplary embodiments of colonoscopy systems having at least one optical source, at least one infrared camera and at least one RGB camera.

FIG. 18 illustrates an exemplary embodiment of the colonoscopy system 10d that includes at least one illuminator 18, and at least one infrared camera 20 and at least one RGB camera 20c. Generally, the optical scanning system 12d includes the illuminator 18 providing structured light in combination with at least one camera 20 (e.g., high resolution NIR cameras), and one RGB camera 20c to produce image data for processing by the control system 16. The illuminator 18 may also include at least one camera optics system 29 (not shown). The optical scanning system 12d may also include the control system 26 (not shown). The optical scanning system 12d may be configured such that the RGB camera 20c may be sensitive to RGB (visible) light which records a visible light image of the tissue under investigation using light emitted by the illuminator 18 and/or light system within the endoscope.

The RGB camera 20c may be configured to capture visible light images of the tissue under investigation using visible light generated by one or more visible light source present in all endoscopic systems 22. The RGB camera 20c may be selected and/or configured to possess the ability to produce full-color, high-resolution images of the tissue under investigation and have both the length and width dimensions that minimize the dimensions of the overall optical scanning system. To produce a sufficiently high-resolution image, an exemplary RGB camera 20c may employ a sensor with a pixel size between 1 µm and 1.4 µm and an array of at least 1900×1900 pixels. The pixel size determines the focal length of the optical scanning system 12d in pixels, according to the equation:

$$f_p = \frac{f_{mm}}{p_{mm}} \qquad \text{(EQ. 10)}$$

where $f_p$ is the focal length in pixels, $f_{mm}$ is the focal length of the optical scanning system 12d in millimeters, and $p_{mm}$ is the pixel size in millimeters. Sensor dimensions may not exceed 4.5 mm×3.5 mm to allow sufficient space for the infrared optical scanning components to achieve sub-millimeter or millimeter accuracy from the triangulation algorithms implemented in the software processing system.

One or more camera optics system 29 (not shown) may be positioned adjacent to the RGB camera 20c to facilitate light collection and to provide the proper field of view to capture images from the entire surface addressed by the optical scanning system 12d. As with the illuminator 18, the camera optics system 29 may include, but is not limited to, a single convex lens or a combination of two or more convex and/or concave lenses.

The geometrical arrangement of the illuminator 18, the high-resolution infrared cameras 20 (e.g., high-resolution infrared cameras), and the RGB cameras 20c may determine the size and resolution of the optical scanning system 12d, with the resolution impacting the measurement accuracy achieved after the processing software produces the three dimensional point cloud. As illustrated in FIG. 18, the high resolution infrared cameras 20 may be positioned on either side of the illuminator 18, and in close proximity. The placement of the RGB camera 20c may include, but is not limited to, between the cameras 20 and next to the illuminator 18, outside the infrared cameras 20 (e.g., high-resolution infrared cameras), and outside the baseline between the cameras 20 and the illuminator 18, for example in an orthogonal direction to the that of the baseline. In some embodiments, the RGB camera 20c may be positioned adjacent to one of the cameras 20 along the same line as the baseline of the infrared scanning components to minimize the size of the optical scanning system 12d.

The geometrical arrangement of the optical scanning system 12d may include, but is not limited to, a parallel configuration and a converged configuration as described in detail herein. The illuminator 18 may be configured to produce a structured light beam that illuminates as much of the combined FOV of the infrared cameras 20 as possible to maximize the area of illuminated tissue recorded. The geometrical arrangement of the infrared components follows that described in the parallel configuration and converged configurations discussed in detail herein.

Figure 19:
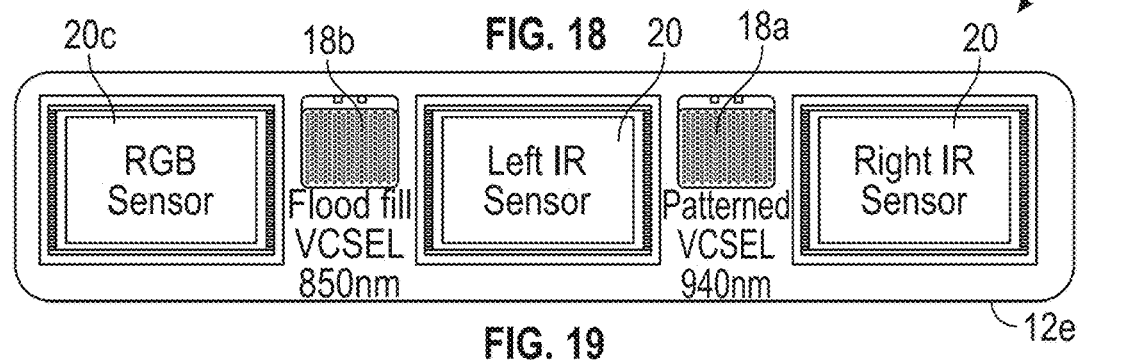

FIG. 19 illustrates another exemplary embodiment of the optical scanning system 12e. Generally, the optical scanning system 12e includes optical components to isolate the infrared scanning components from the components used to capture images for performing registration between three dimensional point clouds. FIG. 19 illustrates an exemplary physical arrangement of the optical scanning system 12e wherein the high-resolution infrared cameras 20 further contain an optical wavelength filter that passes wavelengths above and including 900 nm. The illuminator 18a may be configured to operate at a wavelength that exceeds 900 nm, for example operating at a wavelength of 940 nm. The camera optics system 29 (not shown) associated with the high-resolution RGB camera 20c may be configured to include a wavelength filter that passes only wavelengths below 900 nm, such that the high-resolution RGB camera 20c does not collect light produced by the illuminator 18a. The optical scanning system 12e also includes illuminator 18b, for example a VCSEL-based source, which produces solid (flood) illumination at a wavelength below 900 nm, for example operating at a wavelength of 840 nm. The RGB camera 20c therefore may collects images of illumination provided by the illuminator 18b providing solid (flood) illumination, and the high-resolution infrared cameras 20 may collect images of the structured-light illumination of the tissue produced by the illuminator 18a providing structured illumination. The use of a lower-wavelength solid (flood) illuminator 18b may allow the optical scanning system 12e to take advantage of the higher response from the blood vessels at infrared wavelengths without interference, thus providing higher quality image data to the mapping, registration and modeling component of the software subsystem.

The properties of the components within the illuminator 18, cameras 20 and 20a, camera optics system 29 (not shown), and/or optical imaging system 28 (not shown), the arrangement with respect to each other and the configuration of the complete optical scanning system 12d within the mechanical housing encasing the components determine the performance of the system in terms of lateral and depth resolution, the depth of tissue for which the target resolution is achieved, and the field of view over which the optical scanning system 12d can make measurements.

Generally, the RGB camera 20c captures a visible-light image in the same time frame that the cameras 20 capture infrared images. Specialized analysis software employs triangulation algorithms to associate components of the structured-light pattern recorded in the image of the camera 20 with the corresponding point in the original projected pattern and constructs three dimensional point clouds of the tissue illuminated by the illuminator 18 providing structured light. The software further employs algorithms for matching the patterns of blood vessels recorded by the camera 20 in successive frames in response to the solid illumination source to perform registration and stitch together the three dimensional point clouds to produce three dimensional mappings of the tissue illuminated by the illuminator 18. Additional algorithms utilize the three dimensional point clouds and three dimensional mapping to produce outputs that include, but are not limited to, detection and identification of polyps and adenomas, measurements of height and circumference of the polyps and adenomas, measurement data and other informational icons for augmented displays, and control signals for semi-autonomous and autonomous operation of the endoscopic system.

After producing the three dimensional point cloud of one segment of the illuminated colon tissue, in some embodiments, the colonoscopy system 10d can be used to perform the colonoscopy with the physician moving the optic hardware through the colon and performing a series of independent scans of successive colon segments. The software constructs a three dimensional point cloud representation for each segment and then executes processing algorithms for detecting and measuring polyps and adenomas within each scanned segment. In some embodiments, the software does not attempt to create a three dimensional model of the tissue and does not attempt to stitch together the models or point clouds of each individual segment scanned or to locate each segment within three-dimensional space. As such, no additional sensors to provide feedback regarding the positioning and location of the optical scanning system 12d or 12e may be needed within the colon. In some embodiments, three-dimensional point cloud data collected from the scanning images may be used to provide control signaling needed to implement autonomous or semi-autonomous operation of the endoscope employed in the colonoscopy procedure.

In some embodiments, the physician performing the colonoscopy moves the optical hardware through the colon with the intention of mapping all or part of the colon. The software collects the additional data provided by the unpatterned frames 40 or unpatterned component of composite frames 40, along with data via the AHRS unit 14, in order to stitch together individual images and three dimensional point clouds into a cohesive and accurate model of the colon segment(s) of interest. A minimum level of spatial overlap may exist between images recorded at successive time intervals as the optical scanning system 12d or 12e moves through the colon to allow mapping and registration functions using the unpatterned frames 40 or unpatterned components of composite frames 40. In some embodiments, the optical scanning system 12d or 12e may also employ additional sensors that may include, but are not limited to, other sensors integrated with the optical scanning system 12d or 12e, sensor arrays within the endoscope 22 used in the colonoscopy procedure independent from the optical scanning system 12d or 12e, and/or sensor arrays located externally to the colon or patient that detect signals which allow the software to locate the position of the optical scanning system 12d or 12e within the patient. The additional data provided by the optical scanning system 12d or 12e and the cohesive three dimensional mapping of the colon may provide sufficient information to generate signaling needed to implement autonomous or semi-autonomous operation of the endoscope 22, especially in the colon where the endoscope 22 may need to change shape in the areas behind the scanning head, and support the detection and mitigation of loops in the colon during the colonoscopy procedure.

Referring again to FIG. 1, therein is a block diagram an exemplary control system 16 for use in any of the colonoscopy systems 10-10e and versions thereof. The control system 16 is able to embody and/or execute the logic of the processes described herein. Logic embodied in the form of software instructions and/or firmware may be executed on any appropriate hardware. For example, logic embodied in the form of software instructions and/or firmware may be executed on dedicated system or systems, on distributed processing computer systems, and/or the like. In some embodiments, the logic may be implemented in a stand-alone environment operating on a single system and/or logic may be implemented in a networked environment such as a distributed system using multiple computers and/or processors. For example, microprocessors 90 of the control system 16 may work together or independently to execute processor executable code using one or more memories 92.

FIGS. 20-35 illustrate methods of using the colonoscopy systems 10-10e in further detail. Generally, software within the control system 16 can utilize measurement and imagery data to assist the operator in detecting the existence of a polyp or adenoma within the patient's colon and in measuring the size and dimensions of the polyp, both of which prove critical in identifying and mitigating problems that can later lead to colorectal cancer. If the operator decides to cut a polyp during the colonoscopy procedure, the software can provide imaging data to determine which tool the operator should use to cut the polyp and to provide measurements and positioning data to properly guide and position the tool to ensure the operator removes the entire polyp. At higher levels, software within the control system 16 can utilize the mapping and registration data and modeling functions to assist the operator in identifying the formation of loops within the colon, provide three dimensional mapping of the patient's colon that the operator or the patient's doctor can use to track changes in health over time, and to provide extensive documentation of the entire colonoscopy procedure for later evaluation and analysis. The software, using the mapping and modeling functions to pinpoint the location of the cancerous tissue within the colon in a manner that allows the surgeon to rapidly locate and remove the tissue. The detailed information produced by the software systems allows for the generation of control signals to guide the endoscope 22 through the procedure in either an autonomous or semi-autonomous manner, or to generate augmented displays which assist the operator in guiding current endoscopic tools during a procedure. The autonomous, semi-autonomous, and augmented operating modes may allow, for example, surgeons and other specialists not specifically trained in gastroenterology to perform colonoscopy procedures at a high level and meet the increasing demand for using colonoscopy for both preventative and treatment purposes.

Regarding polyp detection and measurement, the control system 16 may determine a three-dimensional point cloud by extracting from the image data provided by the optical scanning system 12. The three-dimensional point cloud may be used to further: (1) detect the presence of polyps along the wall of the colon; and/or (2) to make measurements on the size of the polyp, including but not limited to the height and the circumference of the polyp. It should be noted that for the optical scanning system 12d and 12e illustrated in FIGS. 18 and 19 respectively, the RGB image provided by the RGB camera 20c may provide an additional method that uses the three dimensional point cloud and a deep-learning engine to detect and measure polyps.

Polyp Detection

Polyp detection may be based on the output from the optical scanning system 12 and utilizes a geometrical analysis method. Generally, there are three operations: modeling, model fitting, and polyp identification.

In the modeling operation, the control system 16 for polyp detection and measurement creates a model of the three-dimensional surface (the set of points in the three dimensional point cloud) by approximating the surface using a set of equations. In the modeling operation, the control system 16 attempts to create a large area model that accurately approximates the geography of the surface over a large scale, instead of modeling accurately every minor variation in the surface structure. By approximating the large scale geometry, the model does not include the variations that correspond to the presence of a polyp along the surface, and this omission in the model may provide means to extract the polyp from the background tissue in the image of the colon wall.

The set of equations used to construct the mathematical model for the modeling operation can include, but is not limited to, a Bezier surface, a splines surface, a surface described by a non-uniform rational B spline (NURBS), and the like. Each mathematical model exhibits strengths and weakness in accurately modeling different types of surfaces, and the process of choosing the best mathematical model for different applications requires the user to test and compare the operation of several mathematical models based on accuracy and successful rate of feature detection in the later functional steps. In what follows the description of the functional operation will assume a NURBS model as a representative example.

The set of equations within a chosen mathematical model contains a set of fitting parameters. The control system 16 for polyp detection and measurement chooses the parameters to allow the equations to best approximate the three dimensional surface through a fitting process. Possible methods for implementing the fitting process include, but are not limited to, an iterative method and a robust method.

In the iterative method, the control system 16 selects an initial set of values for the fitting parameters and measures the accuracy of the approximate surface with respect to the actual surface by methods that include, but are not limited to, average mean square error. The control system 16 may then vary the fitting parameters to minimize the accuracy measurement (for example, minimizing the mean square error). In the iterative method, the number of iterations may be limited, defined as the number of times the method varies the fitting parameters and tests the accuracy, to a small amount to avoid the algorithm from accidentally fitting the surface to a polyp the colonoscopy system 10 wants to detect. Including the polyp in the surface prevents the control system 16 from differentiating the polyp from the background tissue.

An alternative to the iterative method is a robust method. The robust method may be used when the three dimensional point cloud contains a number of different structures and/or when the three dimensional point cloud contains noise, for example. Such methods include, but are not limited to, the Random Sample Consensus (RANSAC) method. The robust method commonly performs good fitting of the large trends in the available data and tends to ignore points that are outliers with respect to the larger trend. For detecting polyps, the outlier points represent the polyps, and therefore exclusion from the fit of the larger surface enhances the performance of the overall polyp detection algorithm in identifying the location of the polyps.

Figure 20A:
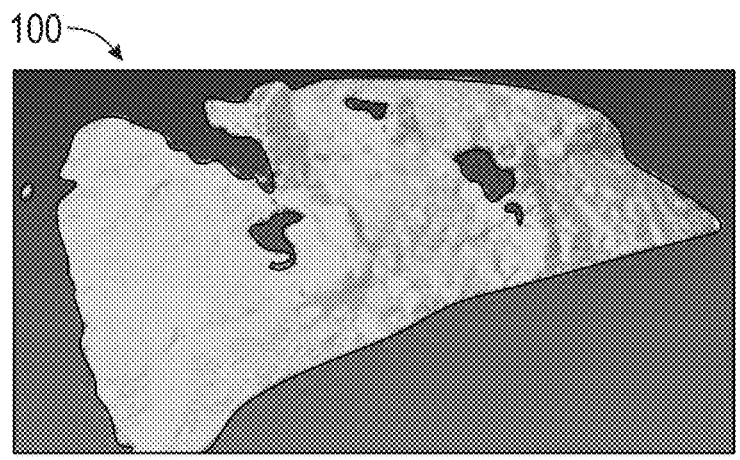
FIGS. 20A and 20B illustrate a three dimensional point cloud obtained from an optical scanning system and an associated outcome of a fitted surface model.
Figure 20B:
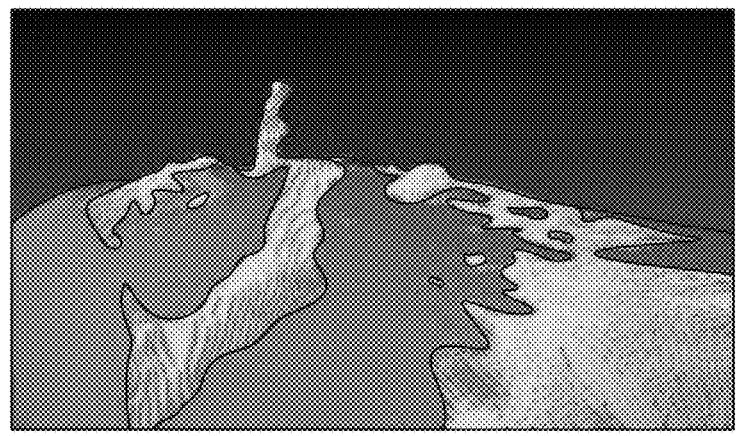

As an example, FIG. 20A shows a three-dimensional point cloud 100 obtained from the optical scanning system 12 (not shown) when scanning a tissue model with simulated polyps. FIG. 20B shows the outcome of fitting the tissue surface using the combination of a NURBS model and the iterative fitting method. In both FIGS. 19(a) and 19(b), the 3D point cloud is colored in yellow. In FIG. 19(b), the fitted surface model is colored in green.

Polyps may be detected via distance map computation and polyp extraction. During distance map computation, the control system 16 creates a spatial map of the distance (or difference in height) between the fitted model and the original three dimensional point cloud. As an example, one method of computing the distance map begins by finding twenty points nearest to a point of interest P. Using only those twenty points, an approximate plane is constructed using a fitting model such as NURBS, and distance is determined between the surface of the plane and the point P along a direction normal to the surface of the plane. For each lateral position along the surface, described by a coordinate pair (x,y), the method stores the computed distance in a matrix. Once the method determines the distance for all points P in the point cloud, a map (or plot) is generated of the computed distance as a function of location. Regions with small values of distance are regions wherein the fitted surface closely approximates the three-dimensional point cloud, and therefore, those regions do not likely contain polyps. Regions with large compute distance represent likely locations in which polyp(s) may exist. For example, FIG. 21 illustrates a computed distance map 110 wherein the regions with higher intensity indicate larger computed distances, and therefore indicate a high likelihood that a polyp exists within the regions.

Figure 21:
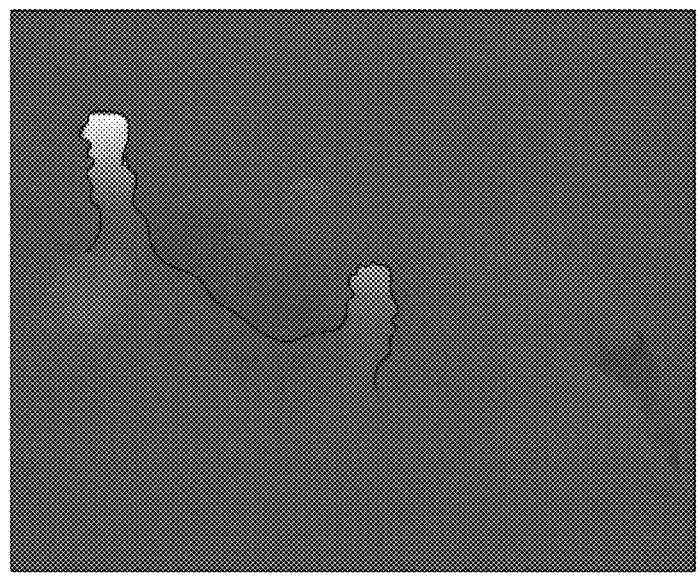
FIG. 21 is a distance map wherein regions with high intensity indicate larger computed distances.

During polyp extraction, the computed distance map 110 in FIG. 21 may be processed to determine the position of possible polyps and to classify the possible polyps as either true polyps that the control system 16 will report or false positives that the control system 16 will reject and not report to the operator. In some embodiments, the data in FIG. 21 passes through a process wherein the continuous data is converted into binary data, with regions over a certain distance labeled as possible polyp sites and other areas labeled as not likely to contain a polyp. These two labels are shown as white pixels and black pixels respectively in FIG. 22A.

After completing the binary processing, the binary image passes through a filtering stage. In the filtering stage, the control system 16 computes the mean intensity, which is proportional to the mean distance, of the region around each possible positive. Regions that produce a mean intensity below a pre-determined threshold intensity are rejected by the filter, leaving only the most likely candidates for polyps for further processing and identification, as shown in FIG. 22B. Training of the control system 16 by an operator or through other means (e.g., artificial intelligence), including but not limited to neural network algorithms, provides the threshold value that maximizes the accuracy of the control system 16 in correctly ignoring false positives. The regions remaining after filtering are then projected back onto the original three dimensional point cloud for further processing, as shown in FIG. 23.

In some embodiments, the next processing step includes, but is not limited to, input of the data in FIG. 23 into a pre-trained artificial intelligence (AI) engine to complete the process of detecting and localizing the polyps. AI engines may include, but are not limited to, supervised AI engines such as a meta heuristic AI engine or an edge key-points detection engine and unsupervised AI engines.

In using edge key-points detection, key points on the depth map are selected that are repeatable (e.g., with respect to noise and local variations) and distinctive (e.g., the area around the keypoint has a unique shape or appearance that a feature extractor can capture). In general, more keypoints used in the algorithm increases the accuracy of polyp detection, and may also increase the processing time required by the algorithm. Proper keypoint selection balances the need for detection accuracy and real-time feedback to the operating physician. Several keypoint algorithms exist in the literature. Proper selection of an algorithm requires experimental verification and testing for a specific application. Each keypoint is described by a vector of values calculated from different feature parameters targeted by the algorithm. The feature parameters selected for the control system 16 for polyp detection and measurement may reflect unique characteristics of the polys compared to nominal features (or lack thereof) of the tissue in the colon wall. The control system 16 computes the feature values and uses a set of weights to classify the keypoint as either part of a polyp or part of the regular surface of the colon wall. The weights are obtained by applying and training a two-class classifier, which include, but are not limited to linear classifiers, decision trees, random forest, neural networks and nearest neighbor. Training occurs on a pre-constructed sample set of data configured to contain all of the cases the trainer expects the classifier to encounter. The training occurs during the original construction of the control system 16, and remains fixed within the software after full system development. An example of the keypoint detection process output is shown in FIG. 24A. All keypoints identified as belonging to a polyp that form an independent cluster are grouped together and labeled as a single polyp, as shown in FIG. 24B. The points allow a second algorithm, including but not limited to an active contour algorithm, to estimate the polyp border, as shown in FIG. 24C.

In using the meta heuristic AI engine (i.e., deep learning AI engine), all of the sub-processes described in the edge key points detection are merged into a single module that performs the entire polyp detection process. This engine requires more training samples and higher processing power to train than the keypoints engine.

In using the unsupervised AI method, training is not required. The method divides the three dimensional point cloud into segments based on geometrical distance, and classifies each segment into a polyp or non-polyp category based on geometrical distance. The segmentation process occurs unsupervised, meaning that the process is not object-aware—the process does not know ahead of time what objects it is looking for. Segmentation algorithms include, but are not limited to, density-based clustering, mean-shift clustering, watershed segmentation, normalized graph cuts, and the like. The process requires tuning of several parameters, of which the most important is the distance function, which describes the distance between each pair of points in the three dimensional point cloud data. Polyp classification uses the geometrical properties of polyps with respect to the background tissue to classify whether a segment belongs to a polyp or to the background tissue. The classification process can occur in an unsupervised or supervised manner.

Post processing may be required to combine segments classified as belonging to a polyp into a single polyp when the segments are directly adjacent to each other. Post processing algorithms include, but are not limited to, active contour format algorithms.

For the colonoscopy systems 10-10d, the software of the control system 16 implements deep learning and artificial intelligence to enhance the accuracy of the results obtained by the colonoscopy system 10-10d. The software combines data from the three dimensional point clouds produced by the optical scanning system 12 and/or three-dimensional mapping from the registration and modeling systems with the visible light data obtained by the RGB camera 20c that the existing endoscopic system 22 uses to provide the physician with images of the surgical procedure. The deep learning and artificial intelligence algorithms reconcile the three dimensional data with the visible light imagery and combine them into an enhanced image that provides additional detail and clear reference points for the location of polyps, adenomas, and other features of interest.

Referring to FIG. 25, for the colonoscopy system 10d or 10e, wherein the RGB camera 20c provides an RGB image, the software implements a deep learning artificial intelligence algorithm to facilitate detection and measurement of polyps, either as a complement to or in lieu of the described method using the output from the infrared scanner only. For the colonoscopy system 10d or 10e, the RGB image and the depth map (i.e., three dimensional point cloud) act as inputs to a polyp detection block that employs deep learning artificial intelligence.

The polyp detector block 111, as shown in FIG. 25 contains a first layer that employs two image processing subnetworks 112 and 114, each tuned with different weights to process the information contained in the depth map 118 and the RGB image 116. A fusion layer 120 works to combine the data obtained from the output of each subnet 112 and 114 into a single set that correlates/maps each component of the depth map 118 to a pixel in the RGB image 116. An artificial intelligence network 122, which can include any of currently known and accepted models and learning techniques, processes the fused data to extract features such as polyps. The artificial intelligence network may be supervised or unsupervised, as described previously.

Poly Measurement

Polyp measurement utilizes output from the detection of polyps via the control system 16 and/or underlying data from the three dimensional point cloud to perform measurements on the polyp. The measurements include, but are not limited to, perimeter and surface area, for example.

The control system 16 may determine the perimeter of the polyp as the sum of distances between successive points along the border of the polyp determined by the polyp detection function, such as that in FIG. 24C. FIG. 26 shows a three dimensional point cloud 130 with the data points 132 located along the polyp border. The control system 16 may use lengths $L_{P1}$, $L_{P2}$ . . . $L_{PN}$ of lines 134 determined between the data points 132 and sum such lengths to calculate the perimeter of the polyp.

In some embodiments, the control system 16 may use one or more curve fitting algorithms to achieve better accuracy in calculating the perimeter. FIG. 27A shows an original shape of a polyp 140 and the data points 142 from a three dimensional point cloud that lie along the original shape. Without knowing the original shape, the control system 16 may estimate distances between the data points using straight lines, as shown in FIG. 27B. The straight line approximation reduces the accuracy of the perimeter calculation as a result. Using one of several available curve-fitting algorithms, control system 16 can add curvature to the lines between the points, as shown in FIG. 27C, resulting in a more natural shape that better matches the original shape. When the polyp measurement function calculates the lengths of the curved lines, a better approximation of the perimeter may be achieved.

In some embodiments, the control system 16 may determine surface area of the polyp. To compute the surface area of the polyp, the control system 16 may collect most or all of the three dimensional point cloud data points 132 that the polyp detection function assigned to a polyp. The control system 16 may form a surface mesh by constructing triangles 136 between sets of three data points 132 along the surface of the three dimensional point cloud data 130, as shown in FIG. 28B. The control system 16 may determine an area of each triangle within the mesh. The control system 16 may determine total surface area by summing the areas of the individual triangles 136.

Referring to FIG. 1, in some embodiments, the control system 16 may provide mapping, registration and modeling during a colonoscopy procedure. Generally, the control system 16 may collect and/or process data from the unstructured (solid) image data and utilize mapping and registration algorithms to align and stitch together three dimensional point clouds into a cohesive, accurate three dimensional model of scanned tissue. The control system 16 may also collect and/or process data from the AHRS unit 14 to provide additional input to the mapping and registration algorithms. The resulting three-dimensional model may provide detection of colon loops, accurate location of features of interest within the length of the colon, construction of baseline models and data of the patient's health, and support semi-autonomous and autonomous operation of the endoscope during a colonoscopy, for example.

For mapping, also referred to as localization, the control system 16 determines position and attitude (orientation) of the optical scanning system 12 at each time an image frame is captured by the camera(s) 20 and/or 20a. For registration, the control system 16 determines the change in position and the change in attitude experienced by the optical scanning system 12 during the time between two images captured by the camera(s) 20 and/or 20a. For mapping, the control system 16, therefore, determines location in space (x, y, z) and angular orientation ($\theta$, $\varphi$, $\psi$) of the optical scanning system 12 at a particular time $t_i$. For registration, the control system 16 may determine difference in location ($\Delta$x, $\Delta$y, $\Delta$z) and the difference in orientation ($\Delta\theta$, $\Delta\varphi$, $\Delta\psi$) of the optical scanning system 12 between the original time $t_i$ and a later time $t_{i+1}$. To accomplish the objective of the control system 16 for mapping and registration, the control system 16 may (a) identify features within the colon that facilitate measurement of the differences in location and orientation and (b) associate captured three dimensional point clouds with specific locations and orientations of the optical scanning system 12.

Identifying Features within the Colon

Generally, there exists a short operating distance between the optical scanning system 12 and the colon wall. Additionally, the surface of the wall tissue may be relatively smooth and featureless. Such features may prohibit use of methods that capture images of a large area around the area targeted for scanning which can overlap significantly between two frames captured at times time $t_i$ and $t_{i+1}$. Additionally, the relatively smooth and featureless surface of the colon wall may provide few opportunities the control system 16 to place markers on clear features that the control system 16 can identify easily in two or more frames.

The colonoscopy system 10 may overcome registration difficulties by capturing and matching patterns of blood vessels within or on the colon wall. To accurately capture and match the patterns of blood vessels, the optical scanning system 12 project an illumination on the wall consisting of more than simply structured light patterns. For the most accurate recovery of the blood vessel patterns, the colonoscopy system 10 may record images that, in whole or in part (composite), contain solid (unpatterned) illumination of the colon wall.

As described in further detail herein in relation to FIGS. 7-17, illumination and capture of images containing solid (unpatterned) illumination of the colon wall may be provided by the illuminator 18 providing an infrared light source and/or the illuminator 18 providing solid illumination. Once the camera(s) 20 capture images of the colon wall illuminated by unpatterned (solid) light, registration between two successive images can be performed by methods that include, but are not limited to, general purpose registration algorithms, algorithm(s) based on generation and matching of binary images, and/or the like.

Figure 29:
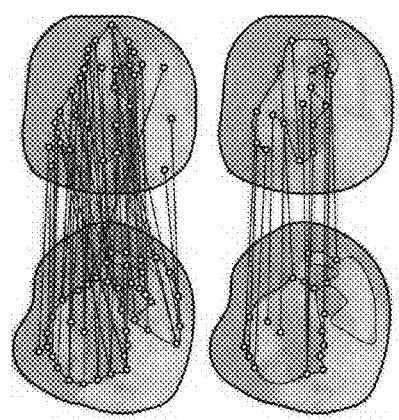
FIG. 29 illustrates images associated with an exemplary method for registration between two successive images.

In some embodiments, general purpose registration algorithms may be used to register data between two successive images as shown in FIG. 29. The general purpose registration algorithms may operate by matching key points that appear in both of the images. The algorithm identifies unique features or points in the original image or frame, and then searches for the same feature or point in the next image or frame.

Figure 30A:
FIGS. 30A and 30B illustrate images associated with an exemplary method for registration of blood vessel structures on a colon wall.
Figure 30B:
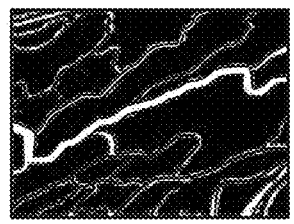

In some embodiments, an algorithm based on the generation and matching of binary images may be used to register data between two successive images as shown in FIGS. 30A and 30B. FIG. 30A illustrates a captured image of blood vessels under unpatterned (solid) illumination. Since the blood vessels represent a unique structure on the colon wall, binarization of the captured image, as shown in FIG. 30B, produces a unique binary (black and white) pattern that simplifies the registration process and makes the process more robust. Modeling of the blood vessels may include, but is not limited to, using a NURBS curve, instead of point-to-point matching, which provides more robust matching than point-to-point matching, for example.

Figure 31A:
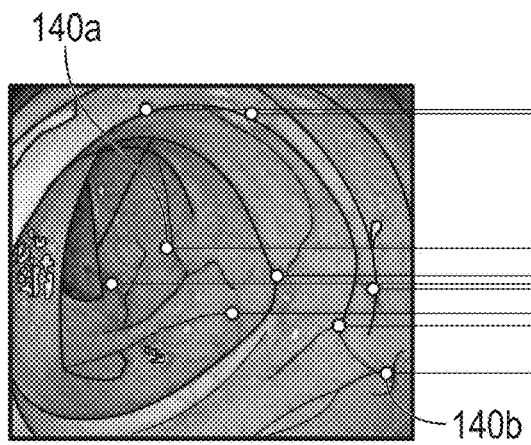
FIGS. 31A, 31B, 32A, and 32B illustrate an exemplary method for registration in a colonoscopy system having the optical scanning systems of FIG. 18 or 19.
Figure 31B:
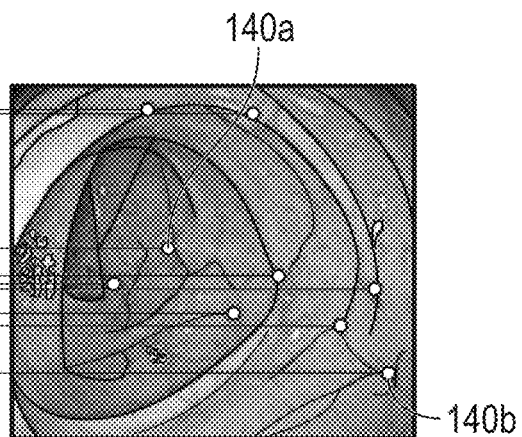
Figure 32A:
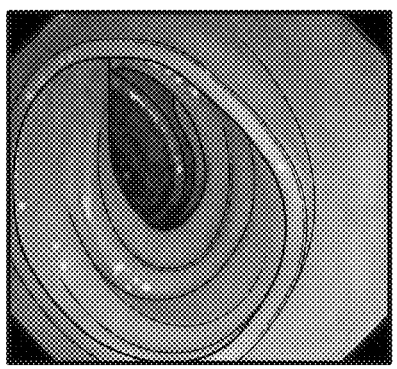
Figure 32B:
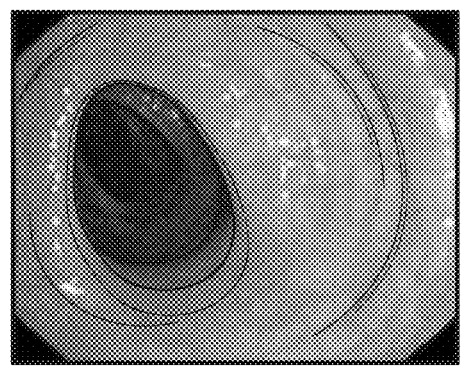

As described in further detail with regard to FIGS. 18 and 19, the colonoscopy system 10 may use the RGB camera 20c to capture full-color, visible light images of the tissue under illumination from the unpatterned visible light source present in all endoscopic systems. Once the RGB camera 20c captures images of the colon wall illuminated by unpatterned (solid) visible light, registration between two successive images can be performed by methods that include, but are not limited general purpose registration algorithms, an algorithm based on generation and matching of binary images similar to that which is described in between above, and/or the like. For example, in some embodiments, general purpose registration algorithms may be used for registration between images and operate by matching key points 140a, 140b . . . 140n that appear in both of the images, as shown in FIGS. 31A and 31B. The algorithm identifies unique features or points in the original image or frame, and then searches for the same feature or point in the next image or frame. For the visible light images when using the RGB camera 20c, for example, the image may require post-processing to ensure that the blood vessels are sufficiently well-defined within the image for the key-point detector to operate effectively. For example, FIG. 32A shows a raw image of the colon wall collected by the RGB camera 20c, in which the blood vessel edges are ill-defined, providing very few features for the key-point detector to detect. Any of several common image processing techniques can produce the image in FIG. 32B, wherein the edges and patterns of the blood vessels appear quite clearly, allowing ready and more accurate extraction of the key points.

Mapping and Registration Between Point Clouds

Mapping and registration may be based on alternating images and mapping and registration based on hybrid images in relation to FIGS. 7-17. In mapping based on alternating images, the optical scanning system 12 may alternately capture images of the colon wall for structure-light (patterned) illumination and unpatterned (solid) illumination. For example, the optical scanning system 12 may illuminate the colon wall with unpatterned (solid) illumination in odd time frames ($t_1$, $t_3$, $t_5$) and illuminate the colon wall with a structured-light pattern in even time frames ($t_2$, $t_4$, $t_6$). During odd time frames, the optical scanning system 12 may capture images of the blood vessel pattern, binarize the images, and perform matching between the two images. The matching process allows the software to estimate the change in position and orientation that occurred in the time between the two frames. During the even time frames, the optical scanning system 12 may capture the structured-light images and the control system 16 may determine the three dimensional point clouds for the colon wall. The control system 16 may estimate the position and orientation of the optical scanning system 12 for the even frames using methods that include, but are not limited to (a) assuming smooth motion of the optical scanning system 12 during the time interval between the odd frames on either side of the even frame, (b) using state-of-the-art point cloud registration algorithms between two successive even frame images, and/or (c) combining data obtained from the odd frames with data obtained via the AHRS unit 14 at every frame (both even and odd). Position and orientation data estimated from the odd frames may be considered to be highly reliable on odd frames and approximate on even frames. Position and orientation data estimated from the AHRS unit 14 may provide only rough accuracy. The accuracy of position and orientation data estimated from the even frames may depend on the number and uniqueness of geometrical features within the captured images.

Figure 33:
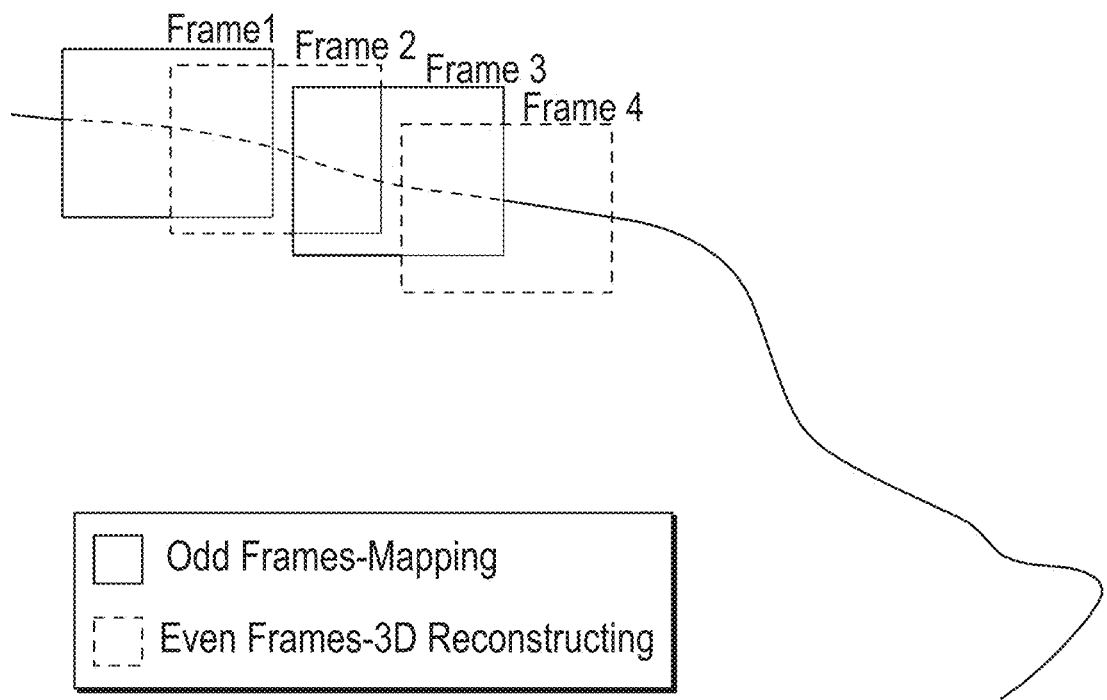
FIGS. 33-34 illustrate an exemplary method for mapping and registration based on alternating images.

Referring to FIG. 33, at Frame 1, the optical scanning system 12 may capture blood vessel images under unpatterned (solid) illumination and orientation data from the AHRS unit 14. At Frame 2, the optical scanning system 12 captures images of the colon wall under structured-light illumination as well as orientation data from the AHRS unit 14, and the control system 16 determines the three dimensional point cloud for the frame. At Frame 3, the optical scanning system 12 captures blood vessel images under unpatterned (solid) illumination and orientation data from the AHRS unit 14, and the control system 16 determines three dimensional between Frames 1 and 3 using the blood vessel markers in Frames 1 and 3 and the orientation data from the AHRS unit 14 from Frames 2 and 3. At Frame 4, the optical scanning system 12 captures images of the colon wall under structured-light illumination, captures orientation data from the AHRS unit 14, and the control system 16 determines the three dimensional point cloud for the frame, and performs registration between Frames 2 and 4 using point clouds from Frames 2 and 4 and the AHRS orientation data from Frames 3 and 4. This process may be repeatable for all following frames.

Figure 34:
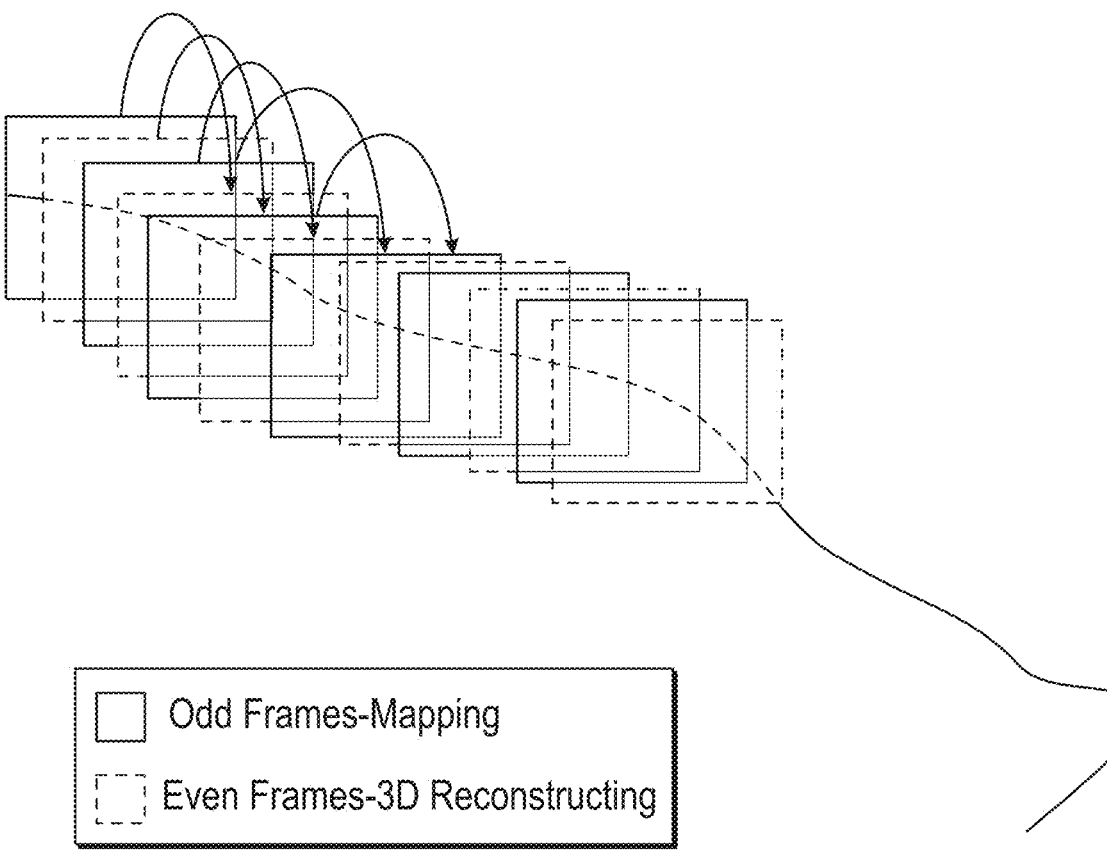

Registration can occur on either a global or semi-global level. For global registration, small errors that accumulate over time may be mitigated by recording images when moving the endoscope 22 into the colon and when moving the endoscope 22 out of the colon. Using images collected on both the inward and outward trips creates a loop that allows elimination or mitigation of the errors. For semi-global registration, registration may be applied to small groups of N sequenced frames that all share some minimal level of mutual information (overlap), as shown in FIG. 34. The use of multiple, semi-global registrations may allow for corrections that ensure better accuracy and less drift in the colonoscopy system 10 over time.

In some embodiments, mapping and registration may be based on hybrid images. For example, the optical scanning system 12 may illuminate the colon wall with a composite or hybrid image containing areas with structured-light illumination and areas with unpatterned (solid) illumination, such as, for example, in FIGS. 6A-6C. The system uses the areas of unpatterned (solid) illumination to capture and perform matching on images of the blood vessel patterns in the colon wall. The control system 16 may use the areas of structured-light illumination to construct one or more three dimensional point clouds of the colon wall.

As an example, at Frame 1, the optical scanning system 12 captures an image of the colon wall illuminated by the hybrid or composite pattern from the illuminator 18 and captures orientation data from the AHRS unit 14. Also at Frame 1, the control system 16 may construct a three dimensional point cloud for the area illuminated by the structured-light pattern and binarizes the blood vessel images collected from the areas illuminated by the unpatterned (solid) illumination. At Frame 2, the optical scanning system 12 captures an image of the colon wall after moving along the colon, captures orientation data from the AHRS unit 14, the control system 16 may construct the point cloud for the area illuminated by the structured-light pattern, and binarizes the blood vessel images collected from the area illuminated by the unpatterned (solid) illumination. The control system 16 may perform two matching processes—one matching process based on the three dimensional point clouds and a second matching based on matching of the binarized blood vessel images. The control system 16 may use results of both matching processes to perform registration between the frames. The process may perform registration between Frames 2 and 3, Frames 3 and 4, and so forth in the same manner.

Mapping and registration for embodiments that include the RGB camera 20c (e.g., embodiments described in relation to FIGS. 18 and 19), may include extraction of three dimensional coordinates, matching between images collected in two consecutive frames, determination of a transformation matrix between matched sets to determine rotation and translation occurring between frames, and global registration.

Calibration data for the RGB camera 20c may allow the control system 16 to determine a transformation matrix between the RGB camera 20c and the structured light infrared camera 20. This transformation matrix may allow the control system 16 to accurately transform the depth map or three dimensional point cloud produced by the infrared scanning components into the frame of reference of the RGB camera 20c, and vice versa, to facilitate mapping. Using the transformation matrix and the depth map, the control system 16 can calculate the three dimensional coordinate [X, Y, Z] of each pixel of the RGB image, and thus can compute the three dimensional coordinate of key points or NURBS curves extracted from the RGB image.

The control system 16 may perform matching between images collected in two consecutive time frames. For the key-point detection approach, the control system 16 may perform matching based on the spatial features contained within the window around the key point. Matching algorithms useful for this process may include, but are not limited to, ORB, SIFT, SURF, and/or KLT. For example, the algorithm for use with consecutive frames may be KLT, as the algorithm proves robust for a consecutive frame approach. For the NURBS curve approach, the control system 16 performs matching between curves. The control system 16 may find a transformation matrix that minimizes the differences between the parameters of the two curves. If such a transformation matrix is found and satisfies the rigidity condition (for example, no changes in the vessel structure occur using the transformation matrix), the two curves are matched.

Once a set of matched key points is identified, the control system 16 may determine the transformation matrix between the matched sets to determine the rotation and translation that occurred between the initial frame and the successive frame. The transformation matrix $T/+^1$ is computed using the equation:

$$\begin{bmatrix} X_1 & X_2 & X_3 \\ Y_1 & Y_2 & Y_3 & \cdots \\ Z_1 & Z_2 & Z_3 \end{bmatrix} = T_i^{i+1} \begin{bmatrix} X'_1 & X'_2 & X'_3 \\ Y'_1 & Y'_2 & Y'_3 & \cdots \\ Z'_1 & Z'_2 & Z'_3 \end{bmatrix} \quad \text{(EQ. 11)}$$

wherein $[X_i, Y_i, Z_i]$ are the coordinates of the matched key points in the initial frame and $[X'_i, Y'_i, Z'_i]$ are the coordinates of the matched key points in the successive frame. Methods for computing the transformation matrix include, but are not limited to, LSE or other linear solving algorithm. To improve the accuracy of the transformation matrix, the computation may also employ algorithms that remove points within the data sets that were incorrectly matched during the matching process. For example, two points representing distinct or different features may be incorrectly identified as representing the same feature and thus removed. Possible solutions include, but are not limited to, robust estimators such as RANSAC, which can greatly improve accuracy of the calculated transformation matrix even if only 40% of the matches produced in the previous step represent valid matched.

For the NURBS curve approach, the process of identifying matches between a pair of curves may produce a transformation matrix, and therefore, a separate transformation matrix determination may not be required. In practice, the process of matching multiple curves between two consecutive frames may result in the determination of multiple transformation matrices. The multiple transformation matrices may not be identical in some or all of the terms. Methods for producing a single transformation matrix for two consecutive frames may include, but are not limited to, averaging the multiple matrices and performing global matching of all the curves simultaneously rather than individually, for example.

Figure 35A:
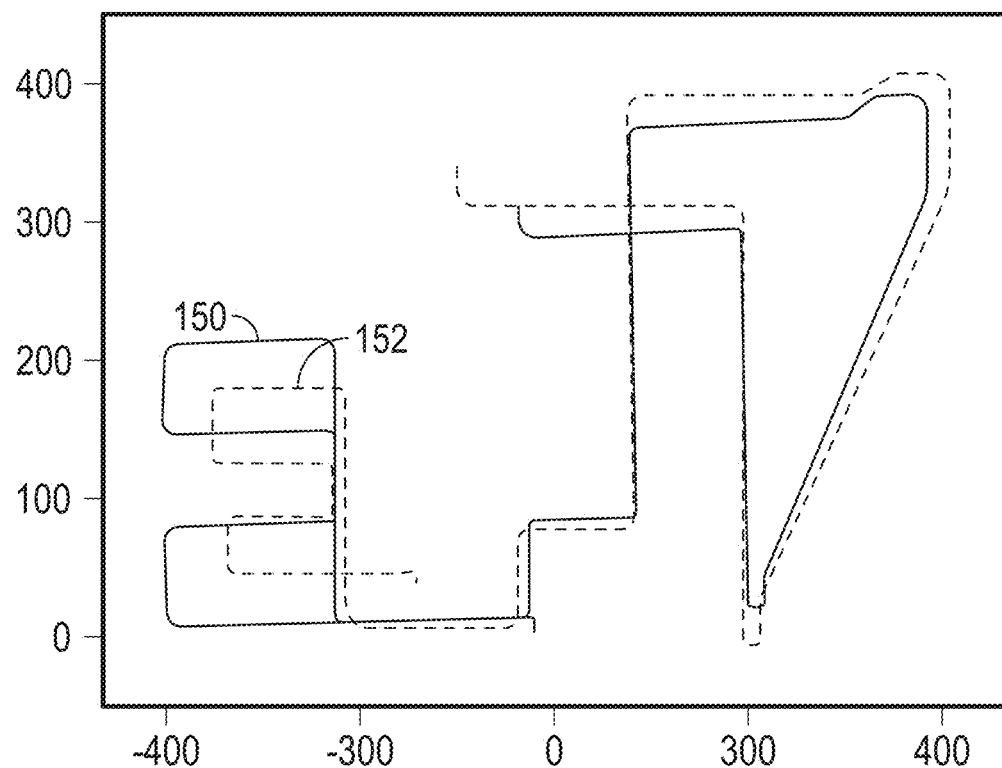
FIGS. 35A and 35B are graphs illustrating comparison of an estimated path and true path of an endoscope during a colonoscopy procedure.
Figure 35B:
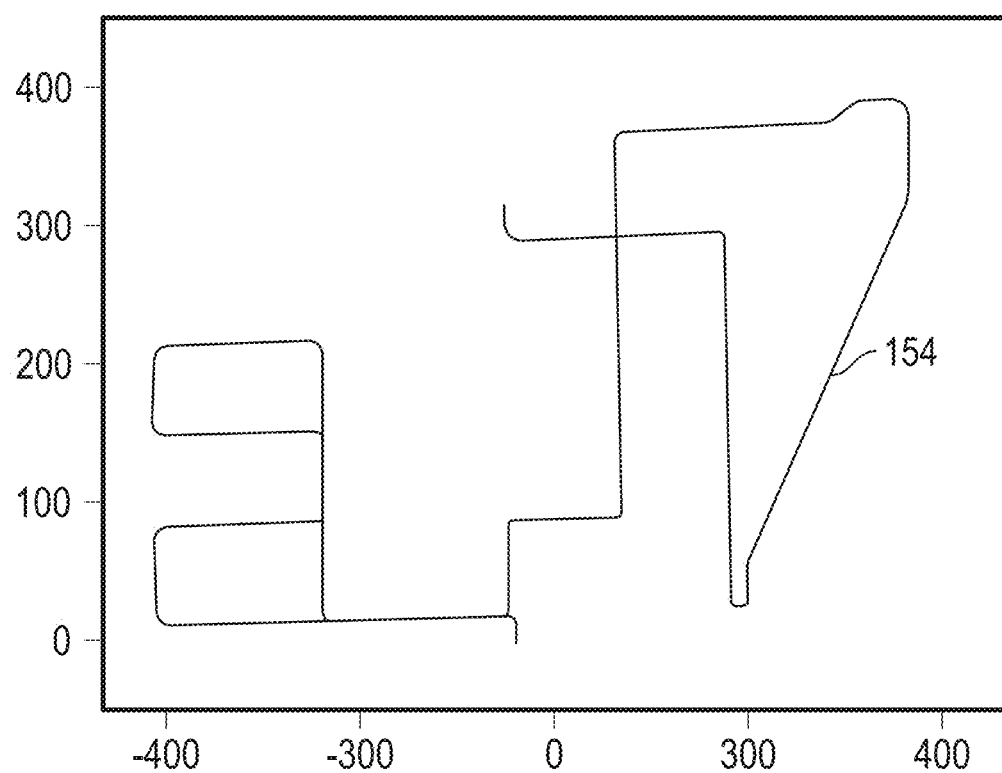

To correct for accumulated error in the registration of consecutive frames over the length of the colon, the control system 16 may perform a global registration process. The control system 16 may periodically label a time frame as a reference frame. For example, the control system 16 may label every 30th frame as a reference frame. The control system 16 stores the key points and descriptor data related to the key points over the entire travel of the endoscope 22. The control system 16 may then performs global registration and/or semi-global registration in a manner similar to that described in FIGS. 33 and 34. FIGS. 35A and 35B illustrate the difference in the computed paths of the endoscope before and after the process of global registration respectively. In FIG. 35A, the line 150 is the estimated path and the line 152 is the true path taken by the endoscope 22. FIG. 35B demonstrates the accuracy of the estimated path 154 attained using global registration methods.

During use the colonoscopy system 10 may provide an operator (e.g., physician) performing a colonoscopy procedure with valuable detection, measurement and analysis tools that enhance the accuracy and effectiveness of the procedure. For example, the colonoscopy system 10 may construct one or more three dimensional point clouds and/or three dimensional models of tissue within the colon, which can contribute to augmented artificial intelligence guidance for the endoscopic operator and further applications in simulation of the procedure for instruction and training. In some embodiments, the colonoscopy system 10 may provide one or more measurements of key features within the scanned volume, including lateral, perimeter, and depth measurements of polyps and adenomas. Knowledge of these parameters may allow an operation (e.g., physician) performing the colonoscopy to make informed decisions (e.g., removal of the polyp or adenoma, selection of proper tool for removal, etc.).

In some embodiments, the colonoscopy system 10 can construct one or more three dimensional models of one or more areas of interest, as well as analyze raw data and the resulting three dimensional point clouds to detect features and/or issues with one or more objects that an operator may miss. For example, the operator may miss a polyp within the colon during a colonoscopy because the polyp is small, visually blends into the background, or is obscured by folds or flaps of tissue in or on the wall of the colon.

In some embodiments, the colonoscopy system 10 may produce three dimensional point clouds and/or three dimensional mapping of a colon wall that can provide image data and/or measurement input to the software processing components to generate some form of alarm or warning system. The alarm or warning system may notify an operator (e.g., physician) when the endoscope approaches too closely to the colon wall, and/or when the orientation, angle, and/or placement of the endoscope within the patient is incorrect. Such an alarm or feedback to the operator may prevent accidental injury to the patient that could potentially occur during the procedure.

The colonoscopy system 10 may provide imagery and/or measurement data of sufficient precision and detail to support development of endoscopic systems with limited to full autonomous operating capabilities. The optical scanning system 12 mounts on or integrates within a head of an endoscope, and may utilize one or more proximity sensors in addition to hardware within the optical scanning system 12. The optical scanning system 12 may be mounted or located in such a way to provide three dimensional point clouds, mapping and registration data, and measurement data for the forward direction and/or along the sides of the head of the endoscope. The control system 16 may utilize the resulting point clouds, mapping and registration data, and measurement data to operate at different levels of autonomy during the colonoscopy procedure. In a semi-autonomous level of operation, the operator may retain primary control of the endoscope, and the control system 16 may provide alarms in some form to warn of potential dangers or errors that could lead to injury to the patient, temporarily take control of the endoscope to avoid such dangers, and provide imagery or other forms of feedback such as augmenting existing displays with relevant data and/or icons, that assists the operator during the task. In a fully autonomous level of operation, the colonoscopy system 10 may exert primary control over the endoscope, using the three dimensional point cloud and measurement data as inputs to control and feedback systems that utilize artificial intelligence techniques to direct the movements of the endoscopic instrument autonomously, within a set of parameters dictated by the operator or the procedure. The operator may retain the ability to override and/or pause the autonomous operation to inspect something of interest to the operator or to perform some operation outside of the main procedure, and then allow the autonomous operation to continue.

For example, colonoscopy procedures require that the endoscope navigate sharp bends in the colon. In either autonomous or semi-autonomous modes of operation, the control system 16 generates a model or map of the surrounding tissue from the three dimensional point cloud and the mapping and registration data collected along the endoscope's route. The operator or control system 16 can utilize the map to control not only the head of the endoscope but also the entire body of the endoscope, ensuring that the shape of the endoscope body conforms to the path through the patient's colon at all times and thus minimizing the chance of causing damage to the patient. The whole endoscope therefore moves autonomously even though the optical scanning system 12 is located only at the head of the endoscope.

FIGS. 36A-36G illustrate an exemplary embodiment of a colonoscopy system 10f in use. An optical scanning system 12f of the colonoscopy system 10f may be incorporated into a colonoscopy instrument currently used within the art. For example, the optical scanning system 12f may include at least one illuminator 18 capable of producing both patterned and solid illumination or combinations (e.g., NIR illumination), and at least one camera 20 integrated directly within an endoscope 22 and the existing endoscope component. The colonoscopy instrument may also include current components found in a colonoscopy system within the art including, but not limited to, a RGB camera, an existing visible light system 160, an air nozzle 161, an instrument channel 162, and/or a water jet 163.

Figure 36A:
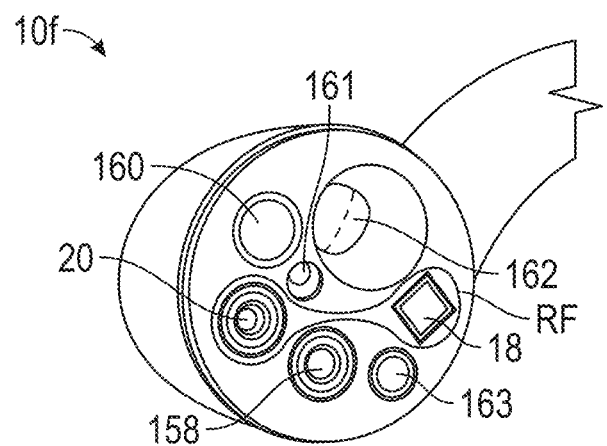
FIGS. 36A-36I illustrate exemplary methods for using an exemplary colonoscopy system in accordance with the present disclosure.
Figure 36B:
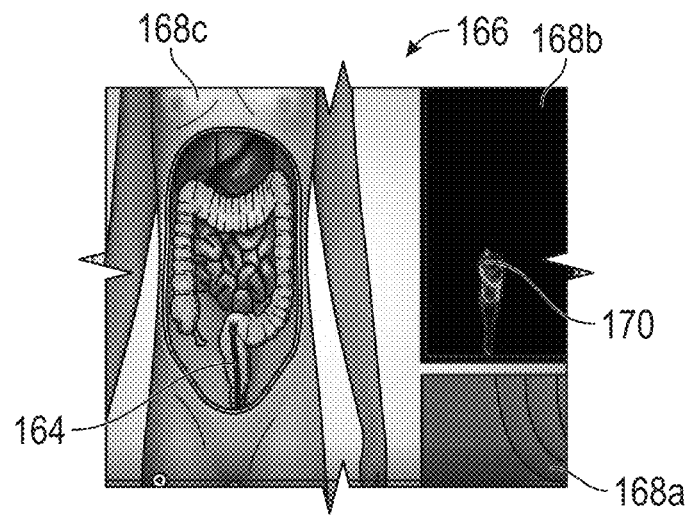

Referring to FIG. 36B, an operator may insert the endoscope 22 into a colon 164. The visible light system 160 is configured to capture one or more visible light images of the colon. The colonoscopy system 10f may provide such visible light images to an operator in any of the common methods used in current colonoscopy systems.

The colonoscopy system 10f may capture three dimensional images and/or two dimensional images of the colon from the NIR cameras 20a and 20b, driven by the illuminator 18 in patterned illumination mode and solid illumination mode, respectively. The control system 16 may use the three dimensional images to construct local three dimensional point clouds and/or three dimensional models, for example. The control system 16 may use the two dimensional images to perform registration calculations and/or stitch the local three dimensional point clouds into one or more three dimensional models of the colon.

The control system 16 may provide output to the operator (e.g., the three dimensional model, measurements, alerts) by one or more output device 166, including, but not limited to, implementations as a an ePaper, computer monitor, speaker, screen, touchscreen, television set, smart phone, PDA, cell phone display, printer, optical head-mounted display, an augmented reality system, combinations thereof, and/or the like. FIG. 36B illustrate the output device 164 as a screen having a plurality of sections 168a-168c for providing information and data to an operator. For example, in some embodiments, at least one section 168a of the output device 166 may provide visible light data or a separate visualization device or screen. In at least one section 168b, the output device 166 may provide a three dimensional model 170 of the colon 164 based on data received by the optical scanning system 12f. The control system 16 may update and add to the three dimensional model 170 presented to the operator in real time after completing each cycle of scanning and processing as described in detail herein.

Figure 36C:
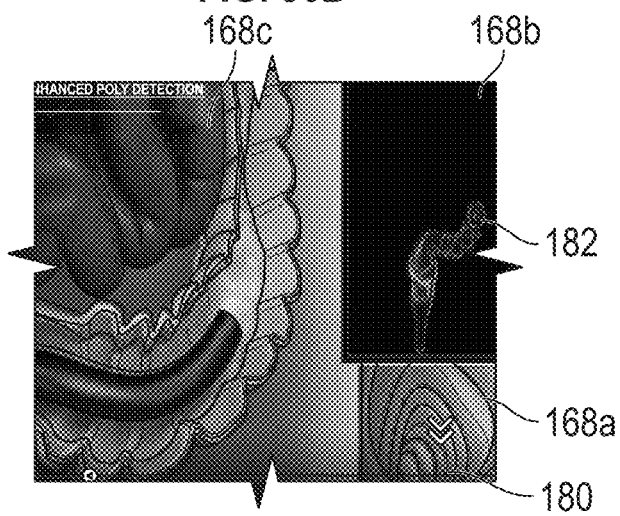
Figure 36D:
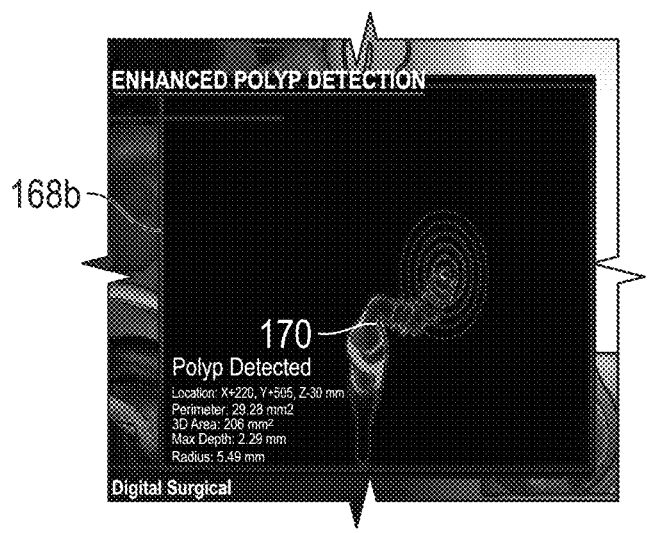

As the endoscope 22 approaches a polyp or feature within the colon 164 (shown as element 180 in the visible light section 168a), the control system 16 using data obtained by the optical scanning system 12f may detect presence of the feature 180 (e.g., polyp). Presence of the feature 180 may be visual, audibly, and/or tactilely provided to the operator. For example, in some embodiments, the operator of the colonoscopy system 10f may alert the operator using methods that include, but are not limited to, visual indicators and/or icons on the three dimensional model in section 168b, augmenting the visible light images in section 168a with icons or other symbols, as shown in FIG. 36C.

Using the registration and model construction capabilities of the three dimensional and/or two dimensional imaging systems, the control system 16 may provide the operator with accurate location, size, and feature information of the feature 180 to the operator. Methods for presenting data regarding location, size, and feature information of the feature 180 to the operator include, but are not limited to, augmenting the visible image (shown in FIG. 36D), displaying the information on the three dimensional colon model, delivering the information to a separate screen or viewing device, and/or a combination thereof.

In some embodiments, the operator can store real time data provided by the control system 16. Stored data may be used in application including, but not limited to, follow-up observations of the feature 180 (e.g., polyp) during later procedures, removal of feature 180 (e.g., polyp removal) in follow-up procedures, maintaining records of patient health, and/or the like.

In practice, residual materials may remain in the colon 164 after preparation procedures, including food remnants and stool. The presence of such residual materials can obscure abnormal tissues from the operator's view, resulting in missed polyps, adenomas, or cancerous growths, or result in the recording of a false positive recording of an abnormal tissue. The colonoscopy system 10f provides the operator with tools to improve correct identification of objects within the colon. For example, if the operator cannot discern whether the feature 180 consists of a polyp, stool, or other residual materials, the operator can use one or more two dimensional images provided by the optical scanning system 12f to reveal whether the object contains or obscures blood vessels. Since a polyp, adenoma, or other abnormal tissue must be fed by blood vessels, an object containing images of blood vessels in the two dimensional image has a high probability of consisting of abnormal tissue. An object for which the two dimensional images do not indicate the presence of blood vessels has a high probability of consisting of stool or other residual materials, as these objects should not contain blood vessels, and will block the blood vessels in the colon 164 from the view of the optical scanning system 12*f*.

Figure 36E:
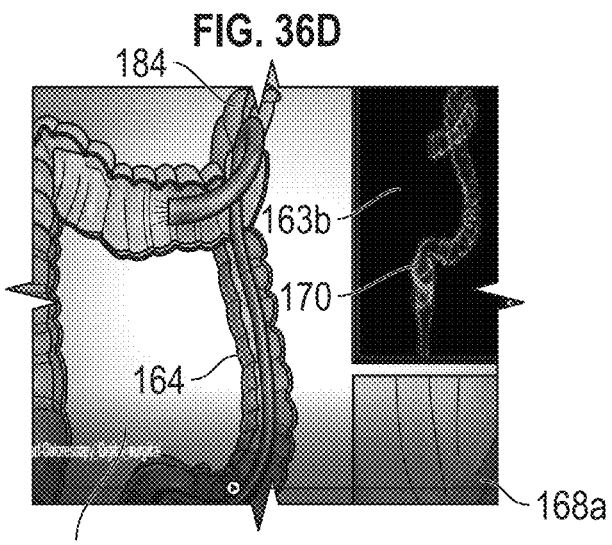

Referring to FIG. 36E, if the colon 164 contains a loop 184 (e.g., alpha loop, reverse alpha loop, N loop, spiral sigmoid loop, or other loop known within the art), the control system 16 can detect the loop 184 from the three dimensional colon model 170. The three dimensional model 170 contains location information for each colon section scanned by the optical scanning system 12*f*. The control system 16 can highlight the loop 184 using methods that include, but are not limited to, changing the color of the three dimensional model 170 in the looped segment, the use of arrows and/or other icons. In the same manner as the detection of features 180, the control system 16 can present data on the exact location of the loop 184 to the operator by methods that include, but are not limited to, augmenting the visible light image with the data, adding data to the three dimensional colon model 170, and/or some combination thereof.

Figure 36F:
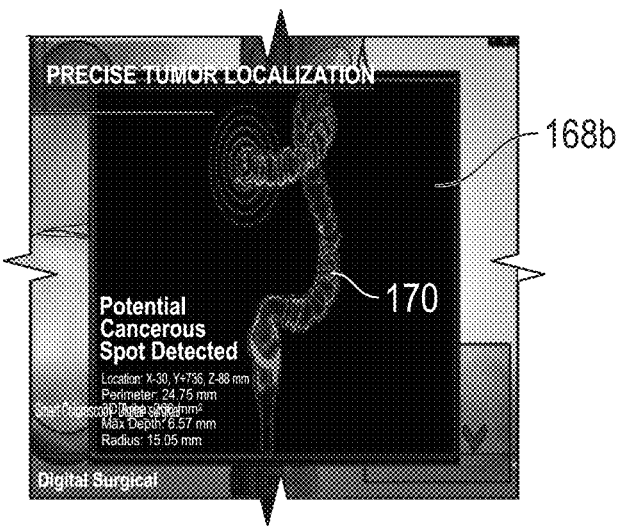

Location data may be relative to a known reference point in space to allow the operator to locate the loop 184 or feature 180 (e.g., polyp or other object within the body of the patient). The reference point may include, but is not limited to, the point of insertion into the body of the patient or any other reference point configurable to the operator. Knowing the exact location of the loop 184, for example, with respect to the reference point in real time may allow the operator to immediately affect treatment of the loop 184 and/or feature 180. Additionally, using methods similar to detection of features 180 and loop 184, the control system 16 can identify the existence of other abnormal tissues, such as a tumor, alert the operator to the presence of the tissue, and provide exact location data to the operator as shown in FIG. 36F. For each, the control system 16 can save location, size and related data in stored memory for later use. Stored memory may include, but not limited to, memory within control system 16 and/or digital record repositories outside of the control system 16 or colonoscopy system 10*f*.

Figure 36G:
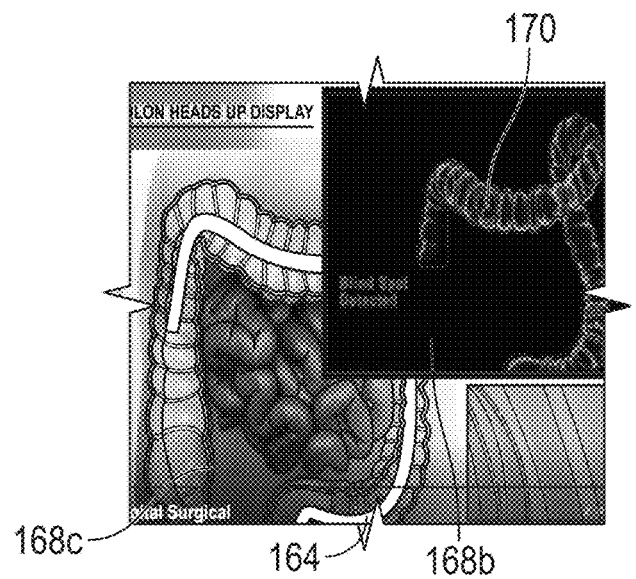

In some embodiments, the operator may navigate the endoscope 22 in such a way that causes the operator to not observe some portion of the colon 164. The continually updated (e.g., dynamic) three dimensional model 170 may, as a result, contain only a partial image of a section of the colon 164. The control system 16 may alert the operator that the optical scanning system 12*f* did not entirely interrogate the section as shown in FIG. 36G. The operator may be alerted by using methods that include, but are not limited to, changing the color of the partially scanned section on the three dimensional colon model 170 and/or augmenting the visible light system images with visual and audible warnings, for example. The alert and the three dimensional colon model 170 may allow the operator to determine the location of the unscanned tissue. The three dimensional model 170 and the visible light imagery provide visual guidance to the operator for maneuvering the endoscope 22 to allow the scanning system to fill in areas that were not originally scanned and did not appear in the three dimensional colon model 170. The visual guidance may include, but is not limited to, the three dimensional model including icons, arrows or other prompts overlaid on the visible light imagery.

Figure 36H:
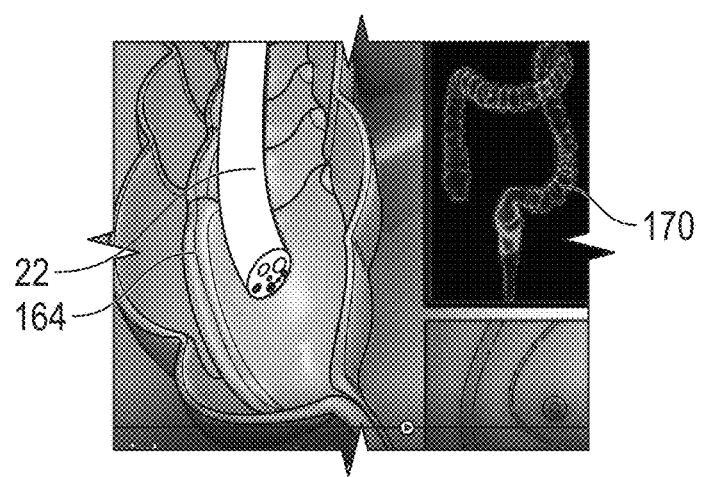
Figure 36I:
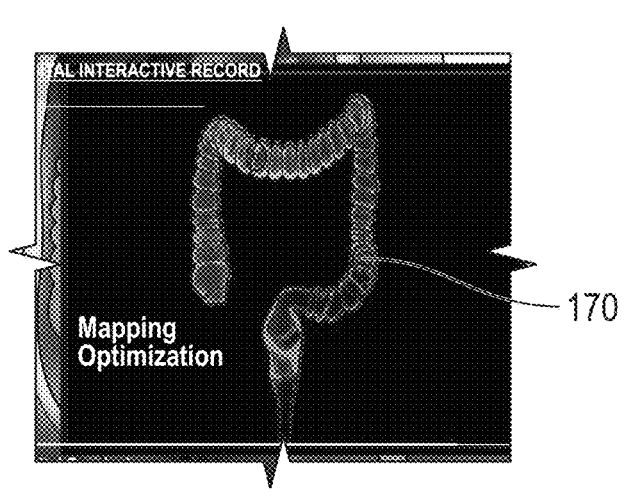

In some embodiments, the three dimensional model 170 may allow the operator to visually verify and officially document that full cecal intubation—complete scanning of the colon 164 to the cecum—did occur, as shown in FIG. 36H. As the operator retracts the endoscope 22 from the patient, the colonoscopy system 10*f* can obtain another scan of each section of the colon 164. Using data related to registration, the control system 16 may update data to and update data within the three dimensional colon model 170. As such, the control system 16 can refine the three dimensional colon model 170, increasing model content and accuracy, refining positions of polyps, adenomas, and tumors, and/or updating any changes in the colon 164. An exemplary update may include, for example, but is not limited to, reimaging the colon 164 after the physician removes the colon loop 184. FIG. 36I depicts the revised three dimensional model 170 of the colon 164, that when compared to FIG. 36E illustrates removal of the colon loop 184.

In some embodiments, the algorithms may allow for the three dimensional model 170 and all imagery augmentation to occur in real-time or substantially real time during the procedure as the optical scanning system 12*f* traverses the colon 164. The operator may be provided with real-time imagery, detection capability, and data in real time or substantially real time.

From the above description, it is clear that the inventive concept(s) disclosed herein are well adapted to carry out the objects and to attain the advantages mentioned herein, as well as those inherent in the inventive concept(s) disclosed herein. While the embodiments of the inventive concept(s) disclosed herein have been described for purposes of this disclosure, it will be understood that numerous changes may be made and readily suggested to those skilled in the art which are accomplished within the scope and spirit of the inventive concept(s) disclosed herein.

The following references are referred to herein.

[1] M. Than, J. Witherspoon, J. Shami, P. Patil, A. Saklani, "Diagnostic miss rate for colorectal cancer: an audit," Annals of Gastroenterology vol. 28, pp. 94-98, 2015

[2] S. B. Ahn, D. S. Han, J. H. Bae, T. J. Byun, J. P. Kim, C. S. Eun, "The miss rate for colorectal adenoma determined by quality-adjusted, back-to-back colonoscopies," Gut and Liver, vol. 6, no. 1, pp. 64-70, 2012.

[3] E. B. Bressler, L. F. Paszat, Z. Chen, D. M. Rothwell, C. Vinden, L. Rabeneck, "Rates of new or missed colorectal cancers after colonoscopy and their risk factors: a population-based analysis," Gastroenterology, vol. 132, no. 1, pp. 96-102, 2007.

[4] A. S. Xirasagar, T. G. Hurley, L. Sros, J. R. Hebert, "Quality and safety of screening colonoscopies performed by primary care physicians with standby specialist support," Med Care, vol. 48, no. 8, pp. 703-709, August 2010.

[5] E. S. Dellon, Q. K. Lippmann, R. S. Sandler, M D, and N. J. Shaheen, "GI endoscopy nurse experience and polyp detection during screening colonoscopy," Clin Gastroenterol Hepatol. 6(12): 1342-1347. December 2008.

[6] C. D. A. Joseph, R. G. S. Meester, A. G. Zauber, D. L. Manninen, L. Winges, F. B. Dong, B. Peaker, M. van Ballegooijen, "Colorectal cancer screening: estimated future colonoscopy need and current volume and capacity," Cancer, p. 2479-2486, August 2016.

[7] American Cancer Society https://www.cancer.org/cancer/colon-rectal-cancer/about/key-statistics.html

[8] B. CDC Vital Signs, "Colorectal Cancer," p. 1-3, July 2011.

[9] NIH National Cancer Institute, Cancer Prevalence and Cost of Care Projections, https://costprojections.cancer.gov/expenditures.html

[10] G. J. Pan, L. Xin, Y.-F. Ma, L.-H. Hu, Z.-S. Li, "Colonoscopy reduces colorectal cancer incidence and mortality in patients with non-malignant findings: a meta-analysis," Am. J. Gastroenterol, vol. 111, pp. 355-365, 2016.

[11] Y. Backes, M. P. Schwartz, F. Borg, F. Wolfhagen, J. Groen, W. Nederveen Cappel, J. Bergeijk, J. Geesing, B. W. M. Spanier, P. Didden, F. Vleggaar, M. M. Lacle, S. Elias, and L. M. G. moons, "Multicentre prospective evaluation of real-time optical diagnosis of T1 colorectal cancer in large non-pedunculated colorectal polyps using narrow band imaging," Endoscopy, BMJ Journals, Vol. 68, Issue 2, 2019.

[12] P. Lefere, S. Gryspeerdt, "Virtual colonoscopy: A practical guide," Springer, 2009.

[13] M. Rubin, L. Lurie, K. Bose, S. H. Kim, "Expanding the view of a standard colonoscope with the third eye panoramic cap," World Journal of Gastroenterology, Vo. 21(37), pp. 10683-10687, 2015.

[14] ASGE Technology Committee, "Endoscopes and devices to improve colon polyp detection," Technology Status Evaluation Report, Gastrointestinal Edoscopy, vol. 81, no. 5, pp. 1122-1129, 2015.

[15] https://endocuff.com/

[16] http://www.smartmedsys.com/index.php/products/naviaid-g-eye/overview

[17] http://www.usendoscopy.com/products/endorings-device

[18] Avanti Medical Systems, https://www.avantismedicalsystems.com/

[19] Shin, Younghak, et al. "Automatic colon polyp detection using region based deep cnn and post learning approaches." IEEE Access 6 (2018): 40950-40962.

[20] Wang, Pu, et al. "Development and validation of a deep-learning algorithm for the detection of polyps during colonoscopy." Nature biomedical engineering 2.10 (2018): 741.

[21] J. W. Leung, A. Thai, A. Yen, G. Ward, O. Abramyan, J Lee, B. Smith, F. Leung, "Magnetic endoscope imaging (ScopeGuide) elucidates the mechanism of action of the pain-alleviating impact of water exchange colonospoy—attenuation of loop formation," J Intery Gastroenterol, Vol 2:3, pp. 142-146, 2012.

[22] Olympus (ScopeGuide), http://medical.olympusamerica.com/technology/scopeguide

[23] Global Market Insights, Endoscopy Market, https://www.gminsights.com/pressrelease/endoscopy-market

[24] Endoscopy Equipment Market by Product and Application Global Forecast, https://www.marketsandmarkets.com/Market-Reports/endoscopy-devices-market-689.html?gclid=CjwKCAiAgrfhBRA3EiwAnfF4tviHObO-MEy-q7SeXyr6FdZrHWBvG08MWCkAadqIxIQNXePADqy2NBoCPKgQAvD_BwE

[25] Olympus, Gastroenterology https://medical.olympusamerica.com/specialty/gastroenterology

[26] Boston Scientific, Gastroenterology http://www.bostonscientific.com/en-US/medical-specialties/gastroenterology.html

[27] Auris health, https://www.aurishealth.com/home.html

[28] P. Zanuttigh, G. Marin, C. D. Mutto, F. Dominio, L. Minto, G. M. Cortelazzo, "Time-of-flight and structured light depth cameras," Chapter 3, Springer 2016.

[29] G. Frankowski, R. Hainich, "DLP-Based 3D metrology by structured light or projected fringe technology for life sciences and industrial metrology," Proceedings of the SPIE, vol. 7210, pp. 72100C-1 to 72100C-12, 2009.

[30] G. Frankowski, R. Hainich, "DLP/DSP-based optical 3D sensors for the mass market in industrial metrology and life sciences," Proceedings of the SPIE, Photonics West, 2011.

[31] J. Geng, "Structured-light 3D surface imaging: a tutorial," Advances in Optics and Photonics, vol. 3, pp. 128-160, 2011.

[32] K. Harding, ed., "Handbook of Optical Dimensional Metrology," CRC Press, Boca Raton, Fla., Chapters 3-5, 2013.

[33] H. Nguyen, D. Nguyen, Z. Wang, H. Kieu, M. Le, "Real-time, high-accuracy 3D imaging and shape measurement," Applied Optics, vol. 54, no. 1, pp. A9-A17, 2015.

[34] Joseph Daniel Bokusky, and Enrique Romo, "Methods and apparatus for constructing endoscopic device with helical lumen design," Auris Surgical Robotics, U.S. Pat. No. 9,844,412, Dec. 19, 2017.

[35] Alan Yu, and Jason Lee, "Articulating flexible endoscopic tool with roll capabilities," Auris Surgical Robotics, U.S. Pat. No. 9,561,083, Feb. 7, 2017.

[36] Mark Harris, "First Surgical Robot from Secretive Startup Auris Cleared for Use," IEEE Spectrum, Jun. 7, 2016.

[37] Alan, Yu, Frederic H. Moll, Benjamin Richter, Mark H. Olson, Jason Gonzalez, Kyle Andrew Tucker, Paxton Maeder-York, and Gregory Schulte, "Surgical robotics system," Auris Surgical Robotics, U.S. Pat. No. 9,622,827, Apr. 18, 2017.

[38] David Mintz, Atiyeh Ghoreyshi, Prasanth Jeevan, Yiliang Xu, Gehua Yang, Mathew Joseph Leotta, Charles Stewart, "Navigation of tubular networks," Auris Surgical Robotics, U.S. Pat. No. 9,727,963, Aug. 8, 2017.

[39] Jeffery Alvarez, Jian Zhang and Alisha Seam, "Method, apparatus and a system for robotics assisted surgery," Auris Surgical Robotics, US 2014/0142591, May 22, 2014.

[40] Jason Lee, Christopher Sramek, Gregory Kintz, David Mintz, and Alan Yu, "Floating electromagnetic field generator system and method of controlling the same," Auris Surgical Robotics, US 2017/0290631, Oct. 12, 2017.

[41] Travis Schuh, Mathew Reagan Williams, Joseph Daniel Bogusky, David Mintz, Alan Yu, and Yoichiro Dan, "Instrument device manipulator with back-mounted tool attachment mechanism," Auris Surgical Robotics, US 2017/0367782, Dec. 28, 2017.

[42] Travis Schuh, "Instrument-mounted tension sending mechanism for robotically-driven medical instruments," Auris Surgical Robotics, U.S. Pat. No. 9,788,910, Oct. 17, 2017.

[43] Travis Schuh, "Instrument device manipulator and surgical drape," Auris Surgical Robotics, U.S. Pat. No. 9,737,373, Aug. 22, 2017.

What is claimed is:

1. A system, comprising:
   at least one optical scanning system configured to scan and capture at least one image of a three-dimensional environment within a colon, the optical scanning system comprising:
   a housing configured to be positioned within the colon and having a proximal end and a distal end, the housing comprising:
   at least one illuminator positioned at the distal end of the housing and configured to produce spatially patterned light and solid light in at least one frame to illuminate tissue within the colon;

at least one camera positioned at the distal end of the housing and configured to capture the at least one image of the illuminated tissue within the colon;

at least one control system configured to construct at least one three dimensional point cloud representations of the tissue within the colon.

2. The system of claim 1, wherein the at least one optical scanning system is within a housing mounted to an endoscopic hardware.

3. The system of claim 1, wherein the housing includes endoscopic hardware and the at least one optical scanning system is integrated within the endoscopic hardware.

4. The system of claim 1, wherein the illuminator includes at least one VCSEL array, at least one projection optic and at least one diffractive optical element.

5. The system of claim 1, wherein the at least one illuminator is configured to produce spatially patterned light and solid light in at least one separate frame.

6. The system of claim 1, wherein the at least one illuminator is configured to produce spatially patterned light and solid light in at least one composite frame.

7. The system of claim 1, wherein operating wavelength of the illuminator producing solid light includes infrared wavelengths configured to resolve blood vessel structures within a wall of the colon; and, wherein the at least one control system is configured to construct the at least one three dimensional point cloud representations of the tissue within the colon via pattern matching between images to extract registration information.

8. The system of claim 1, wherein operating wavelength of the illuminator and the camera includes visible wavelengths.

9. The system of claim 1, wherein the illuminator and camera are configured geometrically and optically to be used with at least one triangulation algorithm configured to provide exact lateral and depth data within size and working distance limitations of the colon.

10. The system of claim 1, wherein the control system uses at least one triangulation algorithm to process data from the camera and illuminator to construct the one or more three dimensional point cloud representations of the tissue within the colon.

11. The system of claim 1, wherein the control system uses data from blood vessel structures within the colon obtained from at least two images of the solid light captured by at least one camera to determine rotation and translation of the optical scanning system between frames.

12. The system of claim 11, wherein the control system uses rotation and translation of the optical scanning system and the at least one three dimensional point cloud representation to provide at least one three dimensional model of the tissue within the colon.

13. The system of claim 12, wherein the three dimensional model traverses an extended length of the colon.

14. The system of claim 13, wherein the extended length of the colon includes an entire length traversed by the optical scanning system through the colon.

15. The system of claim 1, wherein the at least one control system detects presence of a feature within the colon selected from a group consisting of a polyp or an adenoma using the at least one three dimensional point cloud.

16. The system of claim 15, wherein the at least one control system measures the feature within the colon in a lateral and depth dimension.

17. The system of claim 15, wherein the control system provides data to an endoscopic system to autonomously guide positioning of at least one instrument for removal of the feature wherein the control system uses the three dimensional point cloud and measurement data as inputs to control and feedback systems utilizing artificial intelligence techniques to direct movements of the endoscopic system autonomously.

18. The system of claim 1, wherein the control system uses data of the three dimensional point cloud, mapping and registration data to detect and identify loops in the colon.

19. The system of claim 1, wherein the control system uses data of the three dimensional point cloud, mapping and registration data to construct a three-dimensional model of the colon including feature measurement and location data, providing baseline data on health of a patient.

20. The system of claim 1, wherein the control system uses data of the three dimensional point cloud, mapping and registration data to mark location of tissue requiring further analysis.

21. The system of claim 1, wherein the control system further analyzes data of the three dimensional point cloud, mapping and registration data with real time data provided by operation of the optical scanning system within the colon.

22. The system of claim 21, wherein the control system provides at least one alert to an operator of the optical scanning system.

* * * * *